United States Patent [19]
Hercend et al.

[11] Patent Number: 5,874,250
[45] Date of Patent: Feb. 23, 1999

[54] DNA ENCODING FOR A PROTEIN CONTAINING THE EXTRACELLULAR DOMAIN OF LYMPHOCYTE ACTIVATION GENE 3

[75] Inventors: Thierry Hercend, Maisons Alfort; Frédéric Triebel, Neuilly, both of France

[73] Assignees: Institut National de la Sante et de la Recherche Medicale (INSERM), Paris Cedex; Institut Gustave Roussy, Villejuif Cedex, both of France

[21] Appl. No.: 474,988

[22] Filed: Jun. 7, 1995

Related U.S. Application Data

[62] Division of Ser. No. 416,478, Apr. 4, 1995, which is a continuation of Ser. No. 854,644, Sep. 8, 1992, abandoned.

[30] Foreign Application Priority Data

Jan. 8, 1990 [FR] France ................................. 90 00126

[51] Int. Cl.$^6$ .......................... C12N 15/12; C12N 15/19; C12N 15/63; C07H 21/04
[52] U.S. Cl. ..................... 435/69.3; 435/320.1; 435/325; 435/362; 435/365; 435/365.1; 435/367; 435/252.3; 435/252.33; 435/254.11; 536/23.5
[58] Field of Search ................................ 435/69.3, 320.1, 435/325, 362, 365, 365.1, 367, 252.3, 252.33, 254.11; 536/23.5

[56] References Cited

U.S. PATENT DOCUMENTS 5,109,123  4/1992  Reinherz et al. .

FOREIGN PATENT DOCUMENTS 0 329 363  2/1989  European Pat. Off. .
0 320 806  6/1989  European Pat. Off. .

OTHER PUBLICATIONS

Lazar Mol. Cell Biol 8(3):1247–52 Mar. 1988.
Burgess J. Cell Biol 11:2129–38 Nov. 1990.
Triebel, et al., *J. Exp. Med.,* 171:1393–1405, May 1990.
Chang, N.T. et al., *Chemical Abstracts* 102:181–182, 216258n (1985).
Jongstra, J. et al., *J. Exp. Med.* 165:601–614 (1987).
Staunton, D.E. et al., *The EMBO Journal 6(12)*:3695–3701 (1987).
Amzel, L.M. and Poljak, R.J., "Three–Dimensional Structure of Immunoglobulins", *Ann. Rev. Biochem. 48*:961–997 (1979).
Aviv, H. et al., "Purification of Biologically Active Globin Messenger RNA by Chromatography on Oligothymidylic acid–Cellulose", *Proc. Natl. Acad. Sci. USA 69(6)*:1408–1412 (Jun. 1972).
Bowie et al., "Deciphering the Message in Protein Sequences: Tolerance to Amino Acid Substitutions", *Science* 247:1306–1310 (Mar. 1990).

Byrn, R.A. et al., "Biological properties of a CD4 immunoadhesin", *Nature* 334:667–670 (Apr. 12, 1990).
Dariavach P. et al., "Human immunoglobulin $C_\lambda 6$ encodes the Kern $^+$Oz$^-$ λ chain and $C_\lambda 4$ and $C_\lambda 5$ are pseudogenes", *Proc. Natl. Acad. Sci. USA 84*:9074–9078 (Dec. 1987).
Davis, M. M. et al., "Cell–type–specific cDNA probes and the murine I region: The localization and orientation of $A_\alpha{}^a$" *Proc. Natl. Acad. Sci. USA* 81:2194–2198 (Apr. 1984).
Dayhoff, M.O. et al., "Establishing Homologies in Protein Sequences", *Methods Enzymol.* 91:524–45 (1983).
Feinberg, A.P. et al., "A Technique for Radiolabeling DNA Restriction Endonclease Fragments to High Specific Activity", *Anal. Biochem. 132*:6–13 (1983).
Goding, "Production of Monoclonal Antibodies", Chapter 3 in: Goding, Academic Press, *Monoclonal Antibodies: Principles and Practices:*59–103 (1986).
Goding, "Purification, Fragmentation and Isotopic Labelling of Monoclonal Antibodies", Chapter 4 in: Goding, Academic Press, *Monoclonal Antibodies: Principles and Practices:* 104–141 (1986).
Goding, "Generation of Conventional Antibodies", Chapter 8 in: Goding, Academic Press, *Monoclonal Antibodies: Principles and Practices:* 281–293 (1986).
Gubler, U. and Hoffman,B.J., "A simple and very efficient method for generating cDNA libraries", *Gene.* 25:263–269 (1983).
Harris, W.J. et al., "Therapeutic antibodies—the coming of age", *TibTech* 11:42–44 (Feb. 1993).
Hart, C.E. et al., "Human Chromosome 12 is Required for Elevated HIV–1 Expression in Human Haster Hybrid Cells", *Science* 246:488–491 (Oct. 27, 1989).
Huynh, T.V. et al., "Constructing and Screening cDNA Libraries in λgt10 and λgt11" D. Glover (ed), IRL Press. Oxford, UK, *DNA cloning: A practical approach:* 49–78.
Kirszbaum, L. et al., "The α–Chain of Murine CD8 Lacks an Invariant Ig–Like Disulfide Bond but Contains a Unique Intrachain Loop Instead", *J. Immunol. 142(11)*:3931–3936 (Jun. 1, 1989).
Lesk, A.M. and Chothia, C., "Evolution of Proteins Formed by β–Sheets", *J. Mol. Biol. 160*:325–342 (1982).
Luckow, V.A. et al., "Trends in the Development of Baculovirus Expression Vectors", *Bio/Technology* 6:47–55 (Jan. 1988).
Maddon, P.J. et al., "Structure and Expression of the Human and Mouse T4 Genes", *Proc. Natl. Acad. Sci. USA* 84:9155–9159 (1987).
Marlin, S.D. et al., "A soluble form of intercellular adhesion molecule–1 inhibits rhinovirus infection", *Nature* 344:70–72 (Mar. 1, 1990).

(List continued on next page.)

*Primary Examiner*—Anthony C. Caputa
*Attorney, Agent, or Firm*—Browdy and Neimark

[57] ABSTRACT

The present invention relates to a protein containing the extracellular domain of LAG-3, and DNA sequences coding for the protein and the pharmaceutical and biological uses of the protein.

10 Claims, 9 Drawing Sheets

OTHER PUBLICATIONS

Mechler, B. et al., "Membrane–bound Ribosomes of Myeloma Cells IV. mRNA Complexity of Free and Membrane–bound Polysomes", *J. Cell. Biol. 88*:29–36 (Jan. 1981).

Moingeon, P. et al., "A unique T–cell receptor complex expressed on human fetal lymphocytes displaying natural–killer–like activity", *Nature 323*:638–640 (Oct. 16, 1986).

Nowill, A. et al., "Natural Killer Clones Derived From Fetal (25wk) Blood", *J. Exp. Med. 163*:1601–1606 (Jun. 1986).

Ratner, L. et al., "Complete nucleotide sequence of the AIDS virus, HTLV–III", *Nature 313*:277–284 (Jan. 24, 1985).

Ruoslahti, E. et al., "Arg–Gly–Asp: A Versatile Cell Recognition Signal", *Cell 44*:517–518 (Feb. 28, 1986).

Ryu, S.–E. et al., "Crystal structure of an HIV–binding recombinant fragment of human CD4", *Nature 348*:419–426 (Nov. 29, 1990).

Sanger, F. et al., "DNA sequencing with chain–terminating inhibitors", *Proc. Natl. Acad. Sci. USA 74(12)*:5463–7 (Dec. 1977).

Santoni, M.J. et al., "Differential exon usage involving an unusual splicing mechanism generates at least eight types of NCAM cDNA in mouse brain", *EMBO J. 8(2)*:385–392 (1989).

Seed, B., "An LFA–3–cDNA encodes a phospholipid linked membrane protein homologous to its receptor CD2", *Nature 329*:840–842 (Oct. 29, 1987).

Staunton, D.E. et al., "The Arrangement of the Immunoglobulin–like Domains of ICAM–1 and the Binding Sites for LFA–1", *Cell 61*:243–254 (Apr. 20, 1990).

Triebel, F. et al., "Cloned human CD3 ⁻ lymphocytes with natural killer–like activity do not express nor rearrange T cell receptor gamma genes", *Eur. J. Immunol. 17*:1209–1212 (1987).

Waldmann, T. A. et al., "Monoclonal Antibodies in Diagnosis and Therapy", *Science 252*:1657–1662 (Jun. 21, 1991).

Wang, J. et al., "Atomic structure of a fragment of human CD4 containing two immunoglobulin–like domains", *Nature 348*:411–418 (Nov. 29,1990).

Wegner, C.D. et al., "Intercellular Adhesion Molecule–1 (ICAM–1) in the Pathogenesis of Asthma", *Science 247*:456–459 (Jan. 26, 1990).

Williams, A.F., "A year in the life of the immunoglobulin superfamily", *Immunol. Today 8(10)*:298–303 (1987).

Williams, A.F. et al., "The Immunoglobulin Superfamily—Domains for Cell Surface Recognition", *Ann. Rev. Immunol. 6*:381–405 (1988).

Yourno, J. et al., "Nucleotide Sequence Analysis of the env Gene of a New Zairian Isolate of HIV–1", *AIDS Res. Hum. Retroviruses 4(3)*:165–173 (1988).

Ythier, A. et al., "Generation of Monoclonal Antibodies Blocking Cytotoxic Reactions by Human NK Clones: Further Characterization of an 40/80–kDa Target Cell Receptor", *Cell Immunol. 99*:150–159 (1986).

FIG. 5

```
         ...D....     ..E....           ...F...      ....G....        ...A...
 91  RVQLDERGRQRGDFSLWLRPARRADAGEYRAAVHLRDRALSCRLRLRL-GQASMTASPPG
276  GPDLLVTG-DNGDFTLRLEDVSQAQAGTYTCHIHLQEQQLNATVTLAIITVTPKSFGSPG
       .*    *  .  ***.*.*   .*.**  *.   .**... *.   . *  .  .. .  ..**

..         ...B...       ...C...        ....D....       ...E....        ..
150  SLRASDWVILNCSFSRPDRPASVHWFRNRGQGRVPVRESPHHHLAESFLFLPQVSPMDSG
335  SL-----GKLLCEVTPVSGQERFVW--------SSLDTPSQRSFSGPWL-EAQEAQLLSQ
     ,**         *  *    .          *         ..  .... .. .*   *  . . *

..F.....     ....G...
210  PWGCILTYRDGFNVSIM-YNLTVLGLEP..
381  PWQCQL-YQGERLLGAAVY-FTELSS-PGA
     ** * * *..    ..   * .*  *   *
```

FIG. 6

```
                   _____L ___↓_____..A.,    ...B....              ..
LAG-3  MWEAQFLGLLFLQPLWVAPVKPLQPGAEVPVVWAQEGAPAQLPCSPTIPLQDLSLLRR-A
CD4    MCRGFSFRHL-LPLLLLQLSKLLVVTQGKTVVLGKEGGSAELPCESTS--------RRSA
        *  . ** **. †* *  **  ..**..*.*** .*              ** *

..C...    ↓                                  ....C'...  ..C"..   ..
 32    GVTWQHQPDSGPPAAAPGHPLAPGPHPAAPSSWGPRPRRYTVLSVGPGGLRSGRLPLQPR
 25    SFAWKSSDQ-----------------------------KTILGYKNKLLIKGSLELYSR
        . .*.  .                                *.*.    * *  * .*

↑
       ..D....     ...E...        ...F...       .....G....    ↓...A...
 92    VQLDERGRQRGDFSLWLRPARRADAGEYRAAVHLRDRALSCR-LRLRLGQASMTASPPGS
 55    FDSRKNAWERGSFPLIINKLRMEDSQTYVCELENKKEEVELWVFR------VTFNPGTR
        •   ...** *.*  .   *  *. *  ..  . ..*      .* .*
                                                                  ↑
       .   ....B..      ...C...    ....D....    ...E....    .
151    LRASDWVILNCSFSRPDRPASVHWFRNRGQGRVPVRESPHHHLAESFLFLPQVSPM--DS
108    LLQGQSLTLILD-SNPKVSDPPIECKHKSSNIV----------KDSKAFSTH-SLRIQDS
        *  . *  ** ..  *     . ....    *          .*  *  . **

....F....    ...G...↓    ...A...    ...B....       ...
209    GPWGCILTYRDGFNVSIMYNLTVLGLEPP-TPLTVYAGAGSRVGLPCRLPAGVGTRSFLT
156    GIWNCTVTLNQKKHSFDM-KLSVLGFASTSITAYKSEGESAEFSFPLNL--GEES-LQGE
        * *  .*   .  *  .*.****. .        *  . ..* *  *  *
                                    ↑
       .C..                         ....D..    .....E.....   ....
268    AKWTPPG---------------------GGPDLLVTGDNGDFTLRLEDVSQAQAGTYT
212    LRWKAEKAPSSQSWITFSLKNQKVSVQKSTSNPKFQLS-ETLPLTLQIPQVSLQFAGSGN
        .* .                         . *  ...  .**.. .** **.

F.....   ....G....  ↓  ....A..   ...B....      .....C...
305    CHIHLQEQQLNATVTLAIITVTPKSFGSPGSLGKLLCEV-TPVSGQERFVWSSLDTRSQR
371    LTLTLDRGILYQEVNLVVMKVTQ-----PDS-NTLTCEVMGPTSPKMRLILKQENQEARV
        .*.  *   * **  ..  **      *.*   * *** *  * .* *.   . ..
                                    ↑
       ....E.....    ...F....    ...G...    ↓                _____
364    SFSGPWLEAQEAQLLSQPWQCQLYQGERLLGAAVYFTELSSPGAQRSGRAPGALPAGHLL
325    SRQEKVIQVQAPE--AGVWQCLLSEGEEVKMDSKIQV-LSKGLNQ------------TMF
        *    .. * ..    *** *.**  .    † **    *              .

_____TM _____↓  .
424    LFLTLGVL-SLLLLVTGAFGFHLWRRQWRPRRFSALEQGIHPRRLRAR............
370    LAVVLGSAFSFLVF-TGLCILFCVRCRHQQRQAARMSQIK--RLLSEKKTCQCSHRMQKS
        * . **  *.*.. **   .  *  *..**..  *  *       † 
                                                        ↑
427    HNLI
```

Immunoprecipitation of membrane proteins of PHA-blasts well No. 1 : preimmune hetero-antiserum well No. 2 : hetero-antiserum well No. 3 : non-immunoprecipitant Mab well No. 4 : anti-CD2 Mab "Western blot" detection of LAG-3S using a hetero-antiserum in the baculovirus system:

well No. 1 : LAG-3S supernatant well No. 2 : LAG-3S supernatant well No. 3 : AcNPV supernatant well No. 4 : LAG-3S supernatant revealed by a preimmune hetero-antiserum;

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1871 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 231..1724

( x i ) SEQUENCE DESCRIPTION: SEQ ID NO:1:

```
TCAGGCTGCC  TGATCTGCCC  AGCTTTCCAG  CTTTCCTCTG  GATTCCGGCC  TCTGGTCATC         60

CCTCCCCACC  CTCTCTCCAA  GGCCCTCTCC  TGGTCTCCCT  TCTTCTAGAA  CCCCTTCCTC        120

CACCTCCCTC  TCTGCAGAAC  TTCTCCTTTA  CCCCCCACCC  CCCACCACTG  CCCCCTTTCC        180

TTTTCTGACC  TCCTTTTGGA  GGGCTCAGCG  CTGCCCAGAC  CATAGGAGAG  ATG  TGG          236
                                                            Met  Trp
                                                            -28

GAG  GCT  CAG  TTC  CTG  GGC  TTG  CTG  TTT  CTG  CAG  CCG  CTT  TGG  GTG  GCT    284
Glu  Ala  Gln  Phe  Leu  Gly  Leu  Leu  Phe  Leu  Gln  Pro  Leu  Trp  Val  Ala
     -25            Phe            -20                      -15

CCA  GTG  AAG  CCT  CTC  CAG  CCA  GGG  GCT  GAG  GTC  CCG  GTG  GTG  TGG  GCC    332
Pro  Val  Lys  Pro  Leu  Gln  Pro  Gly  Ala  Glu  Val  Pro  Val  Val  Trp  Ala
-10                           -5                     1                    5

CAG  GAG  GGG  GCT  CCT  GCC  CAG  CTC  CCC  TGC  AGC  CCC  ACA  ATC  CCC  CTC    380
Gln  Glu  Gly  Ala  Pro  Ala  Gln  Leu  Pro  Cys  Ser  Pro  Thr  Ile  Pro  Leu
               10                      15                     20

CAG  GAT  CTC  AGC  CTT  CTG  CGA  AGA  GCA  GGG  GTC  ACT  TGG  CAG  CAT  CAG    428
Gln  Asp  Leu  Ser  Leu  Leu  Arg  Arg  Ala  Gly  Val  Thr  Trp  Gln  His  Gln
          25                      30                     35

CCA  GAC  AGT  GGC  CCG  CCC  GCT  GCC  GCC  CCC  GGC  CAT  CCC  CTG  GCC  CCC    476
Pro  Asp  Ser  Gly  Pro  Pro  Ala  Ala  Ala  Pro  Gly  His  Pro  Leu  Ala  Pro
     40                           45                     50

GGC  CCT  CAC  CCG  GCG  GCG  CCC  TCC  TCC  TGG  GGG  CCC  AGG  CCC  CGC  CGC    524
Gly  Pro  His  Pro  Ala  Ala  Pro  Ser  Ser  Trp  Gly  Pro  Arg  Pro  Arg  Arg
55                       60                      65                      70
```

| | | | | | | | | | | | | | | | | |
|---|---|---|---|---|---|---|---|---|---|---|---|---|---|---|---|---|
| TAC | ACG | GTG | CTG | AGC | GTG | GGT | CCC | GGA | GGC | CTG | CGC | AGC | GGG | AGG | CTG | 572 |
| Tyr | Thr | Val | Leu | Ser<br>75 | Val | Gly | Pro | Gly | Gly<br>80 | Leu | Arg | Ser | Gly | Arg<br>85 | Leu | |
| CCC | CTG | CAG | CCC | CGC | GTC | CAG | CTG | GAT | GAG | CGC | GGC | CGG | CAG | CGC | GGG | 620 |
| Pro | Leu | Gln | Pro<br>90 | Arg | Val | Gln | Leu | Asp<br>95 | Glu | Arg | Gly | Arg | Gln<br>100 | Arg | Gly | |
| GAC | TTC | TCG | CTA | TGG | CTG | CGC | CCA | GCC | CGG | CGC | GCG | GAC | GCC | GGC | GAG | 668 |
| Asp | Phe | Ser<br>105 | Leu | Trp | Leu | Arg | Pro<br>110 | Ala | Arg | Arg | Ala | Asp<br>115 | Ala | Gly | Glu | |
| TAC | CGC | GCC | GCG | GTG | CAC | CTC | AGG | GAC | CGC | GCC | CTC | TCC | TGC | CGC | CTC | 716 |
| Tyr | Arg | Ala<br>120 | Ala | Val | His | Leu | Arg<br>125 | Asp | Arg | Ala | Leu | Ser<br>130 | Cys | Arg | Leu | |
| CGT | CTG | CGC | CTG | GGC | CAG | GCC | TCG | ATG | ACT | GCC | AGC | CCC | CCA | GGA | TCT | 764 |
| Arg<br>135 | Leu | Arg | Leu | Gly | Gln<br>140 | Ala | Ser | Met | Thr | Ala<br>145 | Ser | Pro | Pro | Gly | Ser<br>150 | |
| CTC | AGA | GCC | TCC | GAC | TGG | GTC | ATT | TTG | AAC | TGC | TCC | TTC | AGC | CGC | CCT | 812 |
| Leu | Arg | Ala | Ser | Asp<br>155 | Trp | Val | Ile | Leu | Asn<br>160 | Cys | Ser | Phe | Ser | Arg<br>165 | Pro | |
| GAC | CGC | CCA | GCC | TCT | GTG | CAT | TGG | TTC | CGG | AAC | CGG | GGC | CAG | GGC | CGA | 860 |
| Asp | Arg | Pro | Ala<br>170 | Ser | Val | His | Trp | Phe<br>175 | Arg | Asn | Arg | Gly | Gln<br>180 | Gly | Arg | |
| GTC | CCT | GTC | CGG | GAG | TCC | CCC | CAT | CAC | CAC | TTA | GCG | GAA | AGC | TTC | CTC | 908 |
| Val | Pro | Val<br>185 | Arg | Glu | Ser | Pro | His<br>190 | His | His | Leu | Ala | Glu<br>195 | Ser | Phe | Leu | |
| TTC | CTG | CCC | CAA | GTC | AGC | CCC | ATG | GAC | TCT | GGG | CCC | TGG | GGC | TGC | ATC | 956 |
| Phe | Leu | Pro<br>200 | Gln | Val | Ser | Pro | Met<br>205 | Asp | Ser | Gly | Pro | Trp<br>210 | Gly | Cys | Ile | |
| CTC | ACC | TAC | AGA | GAT | GGC | TTC | AAC | GTC | TCC | ATC | ATG | TAT | AAC | CTC | ACT | 1004 |
| Leu | Thr<br>215 | Tyr | Arg | Asp | Gly | Phe<br>220 | Asn | Val | Ser | Ile | Met<br>225 | Tyr | Asn | Leu | Thr<br>230 | |
| GTT | CTG | GGT | CTG | GAG | CCC | CCA | ACT | CCC | TTG | ACA | GTG | TAC | GCT | GGA | GCA | 1052 |
| Val | Leu | Gly | Leu | Glu<br>235 | Pro | Pro | Thr | Pro | Leu<br>240 | Thr | Val | Tyr | Ala | Gly<br>245 | Ala | |
| GGT | TCC | AGG | GTG | GGG | CTG | CCC | TGC | CGC | CTG | CCT | GCT | GGT | GTG | GGG | ACC | 1100 |
| Gly | Ser | Arg | Val<br>250 | Gly | Leu | Pro | Cys | Arg<br>255 | Leu | Pro | Ala | Gly | Val<br>260 | Gly | Thr | |
| CGG | TCT | TTC | CTC | ACT | GCC | AAG | TGG | ACT | CCT | CCT | GGG | GGA | GGC | CCT | GAC | 1148 |
| Arg | Ser | Phe<br>265 | Leu | Thr | Ala | Lys | Trp<br>270 | Thr | Pro | Pro | Gly | Gly<br>275 | Gly | Pro | Asp | |
| CTC | CTG | GTG | ACT | GGA | GAC | AAT | GGC | GAC | TTT | ACC | CTT | CGA | CTA | GAG | GAT | 1196 |
| Leu | Leu<br>280 | Val | Thr | Gly | Asp | Asn<br>285 | Gly | Asp | Phe | Thr | Leu<br>290 | Arg | Leu | Glu | Asp | |
| GTG | AGC | CAG | GCC | CAG | GCT | GGG | ACC | TAC | ACC | TGC | CAT | ATC | CAT | CTG | CAG | 1244 |
| Val | Ser<br>295 | Gln | Ala | Gln | Ala<br>300 | Gly | Thr | Tyr | Thr | Cys<br>305 | His | Ile | His | Leu | Gln<br>310 | |
| GAA | CAG | CAG | CTC | AAT | GCC | ACT | GTC | ACA | TTG | GCA | ATC | ATC | ACA | GTG | ACT | 1292 |
| Glu | Gln | Gln | Leu | Asn<br>315 | Ala | Thr | Val | Thr | Leu<br>320 | Ala | Ile | Ile | Thr | Val<br>325 | Thr | |
| CCC | AAA | TCC | TTT | GGG | TCA | CCT | GGA | TCC | CTG | GGG | AAG | CTG | CTT | TGT | GAG | 1340 |
| Pro | Lys | Ser | Phe<br>330 | Gly | Ser | Pro | Gly | Ser<br>335 | Leu | Gly | Lys | Leu | Leu<br>340 | Cys | Glu | |
| GTG | ACT | CCA | GTA | TCT | GGA | CAA | GAA | CGC | TTT | GTG | TGG | AGC | TCT | CTG | GAC | 1388 |
| Val | Thr | Pro<br>345 | Val | Ser | Gly | Gln | Glu<br>350 | Arg | Phe | Val | Trp | Ser<br>355 | Ser | Leu | Asp | |
| ACC | CCA | TCC | CAG | AGG | AGT | TTC | TCA | GGA | CCT | TGG | CTG | GAG | GCA | CAG | GAG | 1436 |
| Thr | Pro | Ser<br>360 | Gln | Arg | Ser | Phe | Ser<br>365 | Gly | Pro | Trp | Leu | Glu<br>370 | Ala | Gln | Glu | |
| GCC | CAG | CTC | CTT | TCC | CAG | CCT | TGG | CAA | TGC | CAG | CTG | TAC | CAG | GGG | GAG | 1484 |
| Ala | Gln | Leu | Leu | Ser<br>380 | Gln | Pro | Trp | Gln | Cys<br>385 | Gln | Leu | Tyr | Gln | Gly<br>390 | Glu | |

| | | | | | | | | | | | | | | | | |
|---|---|---|---|---|---|---|---|---|---|---|---|---|---|---|---|---|
|AGG|CTT|CTT|GGA|GCA|GCA|GTG|TAC|TTC|ACA|GAG|CTG|TCT|AGC|CCA|GGT|1532|
|Arg|Leu|Leu|Gly|Ala|Ala|Val|Tyr|Phe|Thr|Glu|Leu|Ser|Ser|Pro|Gly| |
| | | | |395| | | |400| | | |405| | | | |
|GCC|CAA|CGC|TCT|GGG|AGA|GCC|CCA|GGT|GCC|CTC|CCA|GCA|GGC|CAC|CTC|1580|
|Ala|Gln|Arg|Ser|Gly|Arg|Ala|Pro|Gly|Ala|Leu|Pro|Ala|Gly|His|Leu| |
| | | |410| | | |415| | | | |420| | | | |
|CTG|CTG|TTT|CTC|ACC|CTT|GGT|GTC|CTT|TCT|CTG|CTC|CTT|TTG|GTG|ACT|1628|
|Leu|Leu|Phe|Leu|Thr|Leu|Gly|Val|Leu|Ser|Leu|Leu|Leu|Leu|Val|Thr| |
| | |425| | | |430| | | | |435| | | | | |
|GGA|GCC|TTT|GGC|TTT|CAC|CTT|TGG|AGA|AGA|CAG|TGG|CGA|CCA|AGA|CGA|1676|
|Gly|Ala|Phe|Gly|Phe|His|Leu|Trp|Arg|Arg|Gln|Trp|Arg|Pro|Arg|Arg| |
| |440| | | |445| | | | |450| | | | | | |
|TTT|TCT|GCC|TTA|GAG|CAA|GGG|ATT|CAC|CCT|CGC|AGG|CTC|AGA|GCA|AGA|1724|
|Phe|Ser|Ala|Leu|Glu|Gln|Gly|Ile|His|Pro|Arg|Arg|Leu|Arg|Ala|Arg| |
|455| | | |460| | | |465| | | | |470| | | |

```
TAGAGGAGCT GGAGCAAGAA CCGGAGCCGG AGCCGGAGCC GGAACCGGAG CCCGAGCCCG    1784

AGCCCGAGCC GGAGCAGCTC TGACCTGGAG CTGAGGCAGC CAGCAGATCT CAGCAGCCCA    1844

GTCCAAATAA ACGTCCTGTC TAGCAGC                                        1871
```

( 2 ) INFORMATION FOR SEQ ID NO:2:

( i ) SEQUENCE CHARACTERISTICS:
        ( A ) LENGTH: 471 amino acids
        ( B ) TYPE: amino acid
        ( D ) TOPOLOGY: linear ( i i ) MOLECULE TYPE: protein ( i x ) FEATURE:
        ( A ) NAME/KEY: Peptide
        ( B ) LOCATION: 1
        ( D ) OTHER INFORMATION: /note= "Hydrogen is present at the
            N- terminus"

( x i ) SEQUENCE DESCRIPTION: SEQ ID NO:2:

| | | | | | | | | | | | | | | |
|---|---|---|---|---|---|---|---|---|---|---|---|---|---|---|
| | | | | | | | | | | Met | Val | Pro | Val | Val |
| | | | | | | | | | | 1 | | | | 5 |
| Trp | Ala | Gln | Glu | Gly | Ala | Pro | Ala | Gln | Leu | Pro | Cys | Ser | Pro | Thr | Ile |
| | | | | 10 | | | | | 15 | | | | | 20 |
| Pro | Leu | Gln | Asp | Leu | Ser | Leu | Leu | Arg | Arg | Ala | Gly | Val | Thr | Trp | Gln |
| | | | | 25 | | | | | 30 | | | | | 35 |
| His | Gln | Pro | Asp | Ser | Gly | Pro | Pro | Ala | Ala | Ala | Pro | Gly | His | Pro | Leu |
| | | | 40 | | | | 45 | | | | | 50 | | |
| Ala | Pro | Gly | Pro | His | Pro | Ala | Ala | Pro | Ser | Ser | Trp | Gly | Pro | Arg | Pro |
| | 55 | | | | | 60 | | | | | 65 | | | | |
| Arg | Arg | Tyr | Thr | Val | Leu | Ser | Val | Gly | Pro | Gly | Leu | Arg | Ser | Gly |
| 70 | | | | | 75 | | | | | 80 | | | | 85 |
| Arg | Leu | Pro | Leu | Gln | Pro | Arg | Val | Gln | Leu | Asp | Glu | Arg | Gly | Arg | Gln |
| | | | | 90 | | | | | 95 | | | | | 100 |
| Arg | Gly | Asp | Phe | Ser | Leu | Trp | Leu | Arg | Pro | Ala | Arg | Arg | Ala | Asp | Ala |
| | | | 105 | | | | | 110 | | | | | 115 | |
| Gly | Glu | Tyr | Arg | Ala | Ala | Val | His | Leu | Arg | Asp | Arg | Ala | Leu | Ser | Cys |
| | | | 120 | | | | | 125 | | | | | 130 | |
| Arg | Leu | Arg | Leu | Arg | Leu | Gly | Gln | Ala | Ser | Met | Thr | Ala | Ser | Pro | Pro |
| | | 135 | | | | | 140 | | | | | 145 | | |
| Gly | Ser | Leu | Arg | Ala | Ser | Asp | Trp | Val | Ile | Leu | Asn | Cys | Ser | Phe | Ser |
| 150 | | | | | 155 | | | | | 160 | | | | | 165 |
| Arg | Pro | Asp | Arg | Pro | Ala | Ser | Val | His | Trp | Phe | Arg | Asn | Arg | Gly | Gln |
| | | | | 170 | | | | | 175 | | | | | 180 |

Gly Arg Val Pro Val Arg Glu Ser Pro His His His Leu Ala Glu Ser
            185                 190                 195

Phe Leu Phe Leu Pro Gln Val Ser Pro Met Asp Ser Gly Pro Trp Gly
            200                 205                 210

Cys Ile Leu Thr Tyr Arg Asp Gly Phe Asn Val Ser Ile Met Tyr Asn
            215                 220                 225

Leu Thr Val Leu Gly Leu Glu Pro Pro Thr Pro Leu Thr Val Tyr Ala
230                         235                 240                 245

Gly Ala Gly Ser Arg Val Gly Leu Pro Cys Arg Leu Pro Ala Gly Val
                250                 255                 260

Gly Thr Arg Ser Phe Leu Thr Ala Lys Trp Thr Pro Pro Gly Gly Gly
            265                 270                 275

Pro Asp Leu Leu Val Thr Gly Asp Asn Gly Asp Phe Thr Leu Arg Leu
            280                 285                 290

Glu Asp Val Ser Gln Ala Gln Ala Gly Thr Tyr Thr Cys His Ile His
            295                 300                 305

Leu Gln Glu Gln Gln Leu Asn Ala Thr Val Thr Leu Ala Ile Ile Thr
310                         315                 320                 325

Val Thr Pro Lys Ser Phe Gly Ser Pro Gly Ser Leu Gly Lys Leu Leu
                330                 335                 340

Cys Glu Val Thr Pro Val Ser Gly Gln Glu Arg Phe Val Trp Ser Ser
            345                 350                 355

Leu Asp Thr Pro Ser Gln Arg Ser Phe Ser Gly Pro Trp Leu Glu Ala
            360                 365                 370

Gln Glu Ala Gln Leu Leu Ser Gln Pro Trp Gln Cys Gln Leu Tyr Gln
            375                 380                 385

Gly Glu Arg Leu Leu Gly Ala Ala Val Tyr Phe Thr Glu Leu Ser Ser
390                         395                 400                 405

Pro Gly Ala Gln Arg Ser Gly Arg Ala Pro Gly Ala Leu Pro Ala Gly
                410                 415                 420

His Leu Leu Leu Phe Leu Thr Leu Gly Val Leu Ser Leu Leu Leu Leu
            425                 430                 435

Val Thr Gly Ala Phe Gly Phe His Leu Trp Arg Arg Gln Trp Arg Pro
            440                 445                 450

Arg Arg Phe Ser Ala Leu Glu Gln Gly Ile His Pro Arg Arg Leu Arg
            455                 460                 465

Ala Arg
470

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:3:

Gly Pro Pro Ala Ala Ala Pro Gly His Pro Leu Ala Pro Gly Pro His
1                   5                   10                  15

Pro Ala Ala Pro Ser Ser Trp Gly Pro Arg Pro Arg Arg Tyr
                20                  25                  30

( 2 ) INFORMATION FOR SEQ ID NO:4:

( i ) SEQUENCE CHARACTERISTICS:
        ( A ) LENGTH: 999 base pairs
        ( B ) TYPE: nucleic acid ( C ) STRANDEDNESS: single
( D ) TOPOLOGY: linear ( x i ) SEQUENCE DESCRIPTION: SEQ ID NO:4:

```
CCTGCAATGT CATTCTTTGA GCTCAGTTCC TCATCTCTGT CATGGAGAGC ATTAGATTTC      60
ATGAATTCAT ACTAAGTGTC CAATACAGTG CTTAGCACGT AATGAAGCCT CAATACAATG     120
TAGTTATTCT CCATGCCCCA CAAAGCTGCA TGCCTAGCCT CAGACCTACC ATTTTTTGGG     180
GTGCAGTAAG GCTTCCTGTC CACCATGTTC CCAGGGACAT TGTACTGATG GGTGGAAAGG     240
CAGGTCTAAA GGGGTCACGA AGTTCTGGGA GGTTAAGGGA ACGAGGAAGG AGATTGAGCA     300
ACAAGGAAAG AGCTTGCCAA GAAGGAGGTG TGAATATTGG GACTGAGGAG GCAGCTTAGA     360
GATGGGCAAG GGGGCAGTTC CAGGCAGAAA TGGTTCGTGG AGGCAGAAGG TCCCTGGGAG     420
AGGGAGCAGT CTGGAGGGTG GGGCAGGGGC GAGGAGGGGG AGGTGGGGAG ACCCAGGACT     480
GAGGAAGTAA ACAAGGGGAG CGCCACCACA GAGGTGGAGA GGTGGAGGGT GCTGCTGCTG     540
GGAATCAACC CCCTCAGACT TTCCACTGCG AAGCGAAACC GTAAGCCCTG GGGTGCGGGG     600
GGCGGGCCGG GAGGAGGGGA AGTGGGGAAG GTGGAGGGAA GGCCGGGCAC AGGGGTGAAG     660
GCCCAGAGAC CAGCAGAACG GCATCCCAGC CACGACGGCC ACTTTGCTCT GTCTGCTGTC     720
CGCCACGGCC CTGCTCTGTT CCCTGGGACA CCCCCGCCCC CACCTCCTCA GGCTGCCTGA     780
TCTGCCCAGC TTTCCAGCTT TCCTCTGGAT TCCGGCCTCT GGTCATCCCT CCCCACCCTC     840
TCTCCAAGGC CCTCTCCTGG TCTCCCTTCT TCTAGAACCC CTTCCTCCAC CTCCCTCTCT     900
GCAGAACTTC TCCTTTCCCC CCACCCCCCA CCACTGCCCC CTTTCCTTTT CTGACCTCCT     960
TTTGGAGGGC TCAGCGCTGC CCAGACCATA GGAGAGATG                            999
```

( 2 ) INFORMATION FOR SEQ ID NO:5:

( i ) SEQUENCE CHARACTERISTICS:
( A ) LENGTH: 1164 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 22..1161

( x i ) SEQUENCE DESCRIPTION: SEQ ID NO:5:

```
GCTGCCCAGA CCATAGGAGA G ATG TGG GAG GCT CAG TTC CTG GGC TTG CTG        51
                         Met Trp Glu Ala Gln Phe Leu Gly Leu Leu
                          1               5                  10

TTT CTG CAG CCG CTT TGG GTG GCT CCA GTG AAG CCT CTC CAG CCA GGG        99
Phe Leu Gln Pro Leu Trp Val Ala Pro Val Lys Pro Leu Gln Pro Gly
             15                  20                  25

GCT GAG GTC CCG GTG GTG TGG GCC CAG GAG GGG GCT CCT GCC CAG CTC       147
Ala Glu Val Pro Val Val Trp Ala Gln Glu Gly Ala Pro Ala Gln Leu
         30                  35                  40

CCC TGC AGC CCC ACA ATC CCC CTC CAG GAT CTC AGC CTT CTG CGA AGA       195
Pro Cys Ser Pro Thr Ile Pro Leu Gln Asp Leu Ser Leu Leu Arg Arg
         45                  50                  55

GCA GGG GTC ACT TGG CAG CAT CAG CCA GAC AGT GGC CCG CCC GCT GCC       243
Ala Gly Val Thr Trp Gln His Gln Pro Asp Ser Gly Pro Pro Ala Ala
         60                  65                  70

GCC CCC GGC CAT CCC CTG GCC CCC GGC CCT CAC CCG GCG GCG CCC TCC       291
Ala Pro Gly His Pro Leu Ala Pro Gly Pro His Pro Ala Ala Pro Ser
    75                  80                  85                  90

TCC TGG GGG CCC AGG CCC CGC CGC TAC ACG GTG CTG AGC GTG GGT CCC       339
Ser Trp Gly Pro Arg Pro Arg Arg Tyr Thr Val Leu Ser Val Gly Pro
```

```
                                      95                              100                                105
GGA   GGC   CTG   CGC   AGC   GGG   AGG   CTG   CCC   CTG   CAG   CCC   CGC   GTC   CAG   CTG       387
Gly   Gly   Leu   Arg   Ser   Gly   Arg   Leu   Pro   Leu   Gln   Pro   Arg   Val   Gln   Leu
                  110                           115                         120

GAT   GAG   CGC   GGC   CGG   CAG   CGC   GGG   GAC   TTC   TCG   CTA   TGG   CTG   CGC   CCA       435
Asp   Glu   Arg   Gly   Arg   Gln   Arg   Gly   Asp   Phe   Ser   Leu   Trp   Leu   Arg   Pro
            125                           130                         135

GCC   CGG   CGC   GCG   GAC   GCC   GGC   GAG   TAC   CGC   GCC   GCG   GTG   CAC   CTC   AGG       483
Ala   Arg   Arg   Ala   Asp   Ala   Gly   Glu   Tyr   Arg   Ala   Ala   Val   His   Leu   Arg
      140                                 145                         150

GAC   CGC   GCC   CTC   TCC   TGC   CGC   CTC   CGT   CTG   CGC   CTG   GGC   CAG   GCC   TCG       531
Asp   Arg   Ala   Leu   Ser   Cys   Arg   Leu   Arg   Leu   Arg   Leu   Gly   Gln   Ala   Ser
155                           160                         165                         170

ATG   ACT   GCC   AGC   CCC   CCA   GGA   TCT   CTC   AGA   GCC   TCC   GAC   TGG   GTC   ATT       579
Met   Thr   Ala   Ser   Pro   Pro   Gly   Ser   Leu   Arg   Ala   Ser   Asp   Trp   Val   Ile
                        175                         180                         185

TTG   AAC   TGC   TCC   TTC   AGC   CGC   CCT   GAC   CGC   CCA   GCC   TCT   GTG   CAT   TGG       627
Leu   Asn   Cys   Ser   Phe   Ser   Arg   Pro   Asp   Arg   Pro   Ala   Ser   Val   His   Trp
                  190                         195                         200

TTC   CGG   AAC   CGG   GGC   CAG   GGC   CGA   GTC   CCT   GTC   CGG   GAG   TCC   CCC   CAT       675
Phe   Arg   Asn   Arg   Gly   Gln   Gly   Arg   Val   Pro   Val   Arg   Glu   Ser   Pro   His
            205                           210                         215

CAC   CAC   TTA   GCG   GAA   AGC   TTC   CTC   TTC   CTG   CCC   CAA   GTC   AGC   CCC   ATG       723
His   His   Leu   Ala   Glu   Ser   Phe   Leu   Phe   Leu   Pro   Gln   Val   Ser   Pro   Met
      220                           225                         230

GAC   TCT   GGG   CCC   TGG   GGC   TGC   ATC   CTC   ACC   TAC   AGA   GAT   GGC   TTC   AAC       771
Asp   Ser   Gly   Pro   Trp   Gly   Cys   Ile   Leu   Thr   Tyr   Arg   Asp   Gly   Phe   Asn
235                           240                         245                         250

GTC   TCC   ATC   ATG   TAT   AAC   CTC   ACT   GTT   CTG   GGT   CTG   GAG   CCC   CCA   ACT       819
Val   Ser   Ile   Met   Tyr   Asn   Leu   Thr   Val   Leu   Gly   Leu   Glu   Pro   Pro   Thr
                        255                         260                         265

CCC   TTG   ACA   GTG   TAC   GCT   GGA   GCA   GGT   TCC   AGG   GTG   GGG   CTG   CCC   TGC       867
Pro   Leu   Thr   Val   Tyr   Ala   Gly   Ala   Gly   Ser   Arg   Val   Gly   Leu   Pro   Cys
                  270                           275                         280

CGC   CTG   CCT   GCT   GGT   GTG   GGG   ACC   CGG   TCT   TTC   CTC   ACT   GCC   AAG   TGG       915
Arg   Leu   Pro   Ala   Gly   Val   Gly   Thr   Arg   Ser   Phe   Leu   Thr   Ala   Lys   Trp
            285                           290                         295

ACT   CCT   CCT   GGG   GGA   GGC   CCT   GAC   CTC   CTG   GTG   ACT   GGA   GAC   AAT   GGC       963
Thr   Pro   Pro   Gly   Gly   Gly   Pro   Asp   Leu   Leu   Val   Thr   Gly   Asp   Asn   Gly
      300                           305                         310

GAC   TTT   ACC   CTT   CGA   CTA   GAG   GAT   GTG   AGC   CAG   GCC   CAG   GCT   GGG   ACC      1011
Asp   Phe   Thr   Leu   Arg   Leu   Glu   Asp   Val   Ser   Gln   Ala   Gln   Ala   Gly   Thr
315                           320                         325                         330

TAC   ACC   TGC   CAT   ATC   CAT   CTG   CAG   GAA   CAG   CAG   CTC   AAT   GCC   ACT   GTC      1059
Tyr   Thr   Cys   His   Ile   His   Leu   Gln   Glu   Gln   Gln   Leu   Asn   Ala   Thr   Val
                        335                         340                         345

ACA   TTG   GCA   ATC   ATC   ACA   GTG   ACT   CCC   AAA   TCC   TTT   GGG   TCA   CCT   GGA      1107
Thr   Leu   Ala   Ile   Ile   Thr   Val   Thr   Pro   Lys   Ser   Phe   Gly   Ser   Pro   Gly
                  350                           355                         360

TCC   TTT   CCT   GGG   ACC   CGG   CAA   GAA   CCA   AAA   ACT   CAC   TCT   CTT   CAA   GGA      1155
Ser   Phe   Pro   Gly   Thr   Arg   Gln   Glu   Pro   Lys   Thr   His   Ser   Leu   Gln   Gly
            365                           370                         375

AAT   CCG   TAA                                                                                     1164
Asn   Pro
      380
```

( 2 ) INFORMATION FOR SEQ ID NO:6:

( i ) SEQUENCE CHARACTERISTICS:
        ( A ) LENGTH: 380 amino acids
        ( B ) TYPE: amino acid (D) TOPOLOGY: linear (ii) MOLECULE TYPE: protein (xi) SEQUENCE DESCRIPTION: SEQ ID NO:6:

```
Met Trp Glu Ala Gln Phe Leu Gly Leu Leu Phe Leu Gln Pro Leu Trp
  1               5                  10                  15
Val Ala Pro Val Lys Pro Leu Gln Pro Gly Ala Glu Val Pro Val Val
                 20                  25                  30
Trp Ala Gln Glu Gly Ala Pro Ala Gln Leu Pro Cys Ser Pro Thr Ile
                 35                  40                  45
Pro Leu Gln Asp Leu Ser Leu Leu Arg Arg Ala Gly Val Thr Trp Gln
                 50                  55                  60
His Gln Pro Asp Ser Gly Pro Pro Ala Ala Ala Pro Gly His Pro Leu
 65                  70                  75                  80
Ala Pro Gly Pro His Pro Ala Ala Pro Ser Ser Trp Gly Pro Arg Pro
                     85                  90                  95
Arg Arg Tyr Thr Val Leu Ser Val Gly Pro Gly Gly Leu Arg Ser Gly
                100                 105                 110
Arg Leu Pro Leu Gln Pro Arg Val Gln Leu Asp Glu Arg Gly Arg Gln
                115                 120                 125
Arg Gly Asp Phe Ser Leu Trp Leu Arg Pro Ala Arg Arg Ala Asp Ala
130                 135                 140
Gly Glu Tyr Arg Ala Ala Val His Leu Arg Asp Arg Ala Leu Ser Cys
145                 150                 155                 160
Arg Leu Arg Leu Arg Leu Gly Gln Ala Ser Met Thr Ala Ser Pro Pro
                165                 170                 175
Gly Ser Leu Arg Ala Ser Asp Trp Val Ile Leu Asn Cys Ser Phe Ser
                180                 185                 190
Arg Pro Asp Arg Pro Ala Ser Val His Trp Phe Arg Asn Arg Gly Gln
                195                 200                 205
Gly Arg Val Pro Val Arg Glu Ser Pro His His His Leu Ala Glu Ser
                210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                245                 250                 255
Leu Thr Val Leu Gly Leu Glu Pro Pro Thr Pro Leu Thr Val Tyr Ala
                260                 265                 270
Gly Ala Gly Ser Arg Val Gly Leu Pro Cys Arg Leu Pro Ala Gly Val
                275                 280                 285
Gly Thr Arg Ser Phe Leu Thr Ala Lys Trp Thr Pro Pro Gly Gly Gly
                290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
                325                 330                 335
Leu Gln Glu Gln Gln Leu Asn Ala Thr Val Thr Leu Ala Ile Ile Thr
                340                 345                 350
Val Thr Pro Lys Ser Phe Gly Ser Pro Gly Ser Phe Pro Gly Thr Arg
                355                 360                 365
Gln Glu Pro Lys Thr His Ser Leu Gln Gly Asn Pro
                370                 375                 380
```

(2) INFORMATION FOR SEQ ID NO:7:

(i) SEQUENCE CHARACTERISTICS:
  (A) LENGTH: 470 amino acids
  (B) TYPE: amino acid
  (D) TOPOLOGY: linear (xi) SEQUENCE DESCRIPTION: SEQ ID NO:7:

```
                                                            Val  Pro  Val  Val
                                                              1
Trp  Ala  Gln  Glu  Gly  Ala  Pro  Ala  Gln  Leu  Pro  Cys  Ser  Pro  Thr  Ile
  5                      10                      15                       20
Pro  Leu  Gln  Asp  Leu  Ser  Leu  Leu  Arg  Arg  Ala  Gly  Val  Thr  Trp  Gln
                     25                      30                      35
His  Gln  Pro  Asp  Ser  Gly  Pro  Pro  Ala  Ala  Ala  Pro  Gly  His  Pro  Leu
                40                      45                      50
Ala  Pro  Gly  Pro  His  Pro  Ala  Ala  Pro  Ser  Ser  Trp  Gly  Pro  Arg  Pro
           55                      60                      65
Arg  Arg  Tyr  Thr  Val  Leu  Ser  Val  Gly  Pro  Gly  Gly  Leu  Arg  Ser  Gly
      70                      75                      80
Arg  Leu  Pro  Leu  Gln  Pro  Arg  Val  Gln  Leu  Asp  Glu  Arg  Gly  Arg  Gln
 85                      90                      95                      100
Arg  Gly  Asp  Phe  Ser  Leu  Trp  Leu  Arg  Pro  Ala  Arg  Arg  Ala  Asp  Ala
                     105                     110                     115
Gly  Glu  Tyr  Arg  Ala  Ala  Val  His  Leu  Arg  Asp  Arg  Ala  Leu  Ser  Cys
                120                     125                     130
Arg  Leu  Arg  Leu  Arg  Leu  Gly  Gln  Ala  Ser  Met  Thr  Ala  Ser  Pro  Pro
           135                     140                     145
Gly  Ser  Leu  Arg  Ala  Ser  Asp  Trp  Val  Ile  Leu  Asn  Cys  Ser  Phe  Ser
     150                     155                     160
Arg  Pro  Asp  Arg  Pro  Ala  Ser  Val  His  Trp  Phe  Arg  Asn  Arg  Gly  Gln
165                     170                     175                      180
Gly  Arg  Val  Pro  Val  Arg  Glu  Ser  Pro  His  His  His  Leu  Ala  Glu  Ser
                     185                     190                     195
Phe  Leu  Phe  Leu  Pro  Gln  Val  Ser  Pro  Met  Asp  Ser  Gly  Pro  Trp  Gly
                200                     205                     210
Cys  Ile  Leu  Thr  Tyr  Arg  Asp  Gly  Phe  Asn  Val  Ser  Ile  Met  Tyr  Asn
           215                     220                     225
Leu  Thr  Val  Leu  Gly  Leu  Glu  Pro  Pro  Thr  Pro  Leu  Thr  Val  Tyr  Ala
     230                     235                     240
Gly  Ala  Gly  Ser  Arg  Val  Gly  Leu  Pro  Cys  Arg  Leu  Pro  Ala  Gly  Val
245                     250                     255                      260
Gly  Thr  Arg  Ser  Phe  Leu  Thr  Ala  Lys  Trp  Thr  Pro  Pro  Gly  Gly  Gly
                     265                     270                     275
Pro  Asp  Leu  Leu  Val  Thr  Gly  Asp  Asn  Gly  Asp  Phe  Thr  Leu  Arg  Leu
                280                     285                     290
Glu  Asp  Val  Ser  Gln  Ala  Gln  Ala  Gly  Thr  Tyr  Thr  Cys  His  Ile  His
           295                     300                     305
Leu  Gln  Glu  Gln  Gln  Leu  Asn  Ala  Thr  Val  Thr  Leu  Ala  Ile  Ile  Thr
     310                     315                     320
Val  Thr  Pro  Lys  Ser  Phe  Gly  Ser  Pro  Gly  Ser  Leu  Gly  Lys  Leu  Leu
325                     330                     335                      340
Cys  Glu  Val  Thr  Pro  Val  Ser  Gly  Gln  Glu  Arg  Phe  Val  Trp  Ser  Ser
                     345                     350                     355
Leu  Asp  Thr  Pro  Ser  Gln  Arg  Ser  Phe  Ser  Gly  Pro  Trp  Leu  Glu  Ala
                360                     365                     370
```

-continued

| Gln | Glu | Ala | Gln | Leu | Leu | Ser | Gln | Pro | Trp | Gln | Cys | Gln | Leu | Tyr | Gln |
|  |  | 375 |  |  |  |  | 380 |  |  |  |  | 385 |  |  |  |

| Gly | Glu | Arg | Leu | Leu | Gly | Ala | Ala | Val | Tyr | Phe | Thr | Glu | Leu | Ser | Ser |
|  | 390 |  |  |  |  | 395 |  |  |  |  | 400 |  |  |  |  |

| Pro | Gly | Ala | Gln | Arg | Ser | Gly | Arg | Ala | Pro | Gly | Ala | Leu | Pro | Ala | Gly |
| 405 |  |  |  |  | 410 |  |  |  |  | 415 |  |  |  |  | 420 |

| His | Leu | Leu | Leu | Phe | Leu | Thr | Leu | Gly | Val | Leu | Ser | Leu | Leu | Leu | Leu |
|  |  |  |  | 425 |  |  |  |  | 430 |  |  |  |  | 435 |  |

| Val | Thr | Gly | Ala | Phe | Gly | Phe | His | Leu | Trp | Arg | Arg | Gln | Trp | Arg | Pro |
|  |  |  | 440 |  |  |  |  | 445 |  |  |  |  | 450 |  |  |

| Arg | Arg | Phe | Ser | Ala | Leu | Glu | Gln | Gly | Ile | His | Pro | Arg | Arg | Leu | Arg |
|  |  | 455 |  |  |  |  | 460 |  |  |  |  | 465 |  |  |  |

| Ala | Arg |
|  | 470 |

( 2 ) INFORMATION FOR SEQ ID NO:8:

( i ) SEQUENCE CHARACTERISTICS:
        ( A ) LENGTH: 457 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

| Met | Cys | Arg | Gly | Phe | Ser | Phe | Arg | His | Leu | Leu | Pro | Leu | Leu | Leu | Leu |
| 1 |  |  |  | 5 |  |  |  |  | 10 |  |  |  |  | 15 |  |

| Gln | Leu | Ser | Lys | Leu | Leu | Val | Val | Thr | Gln | Gly | Lys | Thr | Val | Val | Leu |
|  |  |  | 20 |  |  |  |  | 25 |  |  |  |  | 30 |  |  |

| Gly | Lys | Glu | Gly | Gly | Ser | Ala | Glu | Leu | Pro | Cys | Glu | Ser | Thr | Ser | Arg |
|  |  | 35 |  |  |  |  | 40 |  |  |  |  | 45 |  |  |  |

| Arg | Ser | Ala | Ser | Phe | Ala | Trp | Lys | Ser | Ser | Asp | Gln | Lys | Thr | Ile | Leu |
|  | 50 |  |  |  |  | 55 |  |  |  |  | 60 |  |  |  |  |

| Gly | Tyr | Lys | Asn | Lys | Leu | Leu | Ile | Lys | Gly | Ser | Leu | Glu | Leu | Tyr | Ser |
| 65 |  |  |  |  | 70 |  |  |  |  | 75 |  |  |  |  | 80 |

| Arg | Phe | Asp | Ser | Arg | Lys | Asn | Ala | Trp | Glu | Arg | Gly | Ser | Phe | Pro | Leu |
|  |  |  |  | 85 |  |  |  |  | 90 |  |  |  |  | 95 |  |

| Ile | Ile | Asn | Lys | Leu | Arg | Met | Glu | Asp | Ser | Gln | Thr | Tyr | Val | Cys | Glu |
|  |  |  | 100 |  |  |  |  | 105 |  |  |  |  | 110 |  |  |

| Leu | Glu | Asn | Lys | Lys | Glu | Glu | Val | Glu | Leu | Trp | Val | Phe | Arg | Val | Thr |
|  |  |  | 115 |  |  |  |  | 120 |  |  |  |  | 125 |  |  |

| Phe | Asn | Pro | Gly | Thr | Arg | Leu | Leu | Gln | Gly | Gln | Ser | Leu | Thr | Leu | Ile |
|  |  | 130 |  |  |  |  | 135 |  |  |  |  | 140 |  |  |  |

| Leu | Asp | Ser | Asn | Pro | Lys | Val | Ser | Asp | Pro | Pro | Ile | Glu | Cys | Lys | His |
| 145 |  |  |  |  | 150 |  |  |  |  | 155 |  |  |  |  | 160 |

| Lys | Ser | Ser | Asn | Ile | Val | Lys | Asp | Ser | Lys | Ala | Phe | Ser | Thr | His | Ser |
|  |  |  |  | 165 |  |  |  |  | 170 |  |  |  |  | 175 |  |

| Leu | Arg | Ile | Gln | Asp | Ser | Gly | Ile | Trp | Asn | Cys | Thr | Val | Thr | Leu | Asn |
|  |  |  | 180 |  |  |  |  | 185 |  |  |  |  | 190 |  |  |

| Gln | Lys | Lys | His | Ser | Phe | Asp | Met | Lys | Leu | Ser | Val | Leu | Gly | Phe | Ala |
|  |  | 195 |  |  |  |  | 200 |  |  |  |  | 205 |  |  |  |

| Ser | Thr | Ser | Ile | Thr | Ala | Tyr | Lys | Ser | Glu | Gly | Glu | Ser | Ala | Glu | Phe |
|  | 210 |  |  |  |  | 215 |  |  |  |  | 220 |  |  |  |  |

| Ser | Phe | Pro | Leu | Asn | Leu | Gly | Glu | Glu | Ser | Leu | Gln | Gly | Glu | Leu | Arg |
| 225 |  |  |  |  | 230 |  |  |  |  | 235 |  |  |  |  | 240 |

| Trp | Lys | Ala | Glu | Lys | Ala | Pro | Ser | Ser | Gln | Ser | Trp | Ile | Thr | Phe | Ser |

245                                    250                                    255

Leu    Lys    Asn    Gln    Lys    Val    Ser    Val    Gln    Lys    Ser    Thr    Ser    Asn    Pro    Lys
                             260                           265                           270

Phe    Gln    Leu    Ser    Glu    Thr    Leu    Pro    Leu    Thr    Leu    Gln    Ile    Pro    Gln    Val
                      275                           280                           285

Ser    Leu    Gln    Phe    Ala    Gly    Ser    Gly    Asn    Leu    Thr    Leu    Thr    Leu    Asp    Arg
                      290                           295                           300

Gly    Ile    Leu    Tyr    Gln    Glu    Val    Asn    Leu    Val    Val    Met    Lys    Val    Thr    Gln
        305                                 310                           315                                  320

Pro    Asp    Ser    Asn    Thr    Leu    Thr    Cys    Glu    Val    Met    Gly    Pro    Thr    Ser    Pro
                                    325                           330                           335

Lys    Met    Arg    Leu    Ile    Leu    Lys    Gln    Glu    Asn    Gln    Glu    Ala    Arg    Val    Ser
                             340                           345                           350

Arg    Gln    Glu    Lys    Val    Ile    Gln    Val    Gln    Ala    Pro    Glu    Ala    Gly    Val    Trp
                      355                           360                           365

Gln    Cys    Leu    Leu    Ser    Glu    Gly    Glu    Val    Lys    Met    Asp    Ser    Lys    Ile
                      370                           375                           380

Gln    Val    Leu    Ser    Lys    Gly    Leu    Asn    Gln    Thr    Met    Phe    Leu    Ala    Val    Val
        385                                 390                           395                                  400

Leu    Gly    Ser    Ala    Phe    Ser    Phe    Leu    Val    Phe    Thr    Gly    Leu    Cys    Ile    Leu
                                    405                           410                           415

Phe    Cys    Val    Arg    Cys    Arg    His    Gln    Gln    Arg    Gln    Ala    Ala    Arg    Met    Ser
                             420                           425                           430

Gln    Ile    Lys    Arg    Leu    Leu    Ser    Glu    Lys    Lys    Thr    Cys    Gln    Cys    Ser    His
                      435                           440                           445

Arg    Met    Gln    Lys    Ser    His    Asn    Leu    Ile
        450                                 455

( 2 ) INFORMATION FOR SEQ ID NO:9:

( i ) SEQUENCE CHARACTERISTICS:
         ( A ) LENGTH: 498 amino acids
         ( B ) TYPE: amino acid
         ( C ) STRANDEDNESS: single
         ( D ) TOPOLOGY: linear ( i i ) MOLECULE TYPE: protein ( x i ) SEQUENCE DESCRIPTION: SEQ ID NO:9:

Met    Trp    Glu    Ala    Gln    Phe    Leu    Gly    Leu    Leu    Phe    Leu    Gln    Pro    Leu    Trp
        1                            5                            10                                   15

Val    Ala    Pro    Val    Lys    Pro    Leu    Gln    Pro    Gly    Ala    Glu    Val    Pro    Val    Val
                             20                           25                            30

Trp    Ala    Gln    Glu    Gly    Ala    Pro    Ala    Gln    Leu    Pro    Cys    Ser    Pro    Thr    Ile
                      35                           40                            45

Pro    Leu    Gln    Asp    Leu    Ser    Leu    Leu    Arg    Arg    Ala    Gly    Val    Thr    Trp    Gln
                      50                           55                            60

His    Gln    Pro    Asp    Ser    Gly    Pro    Pro    Ala    Ala    Ala    Pro    Gly    His    Pro    Leu
        65                                  70                            75                                    80

Ala    Pro    Gly    Pro    His    Pro    Ala    Ala    Pro    Ser    Ser    Trp    Gly    Pro    Arg    Pro
                                    85                            90                                   95

Arg    Arg    Tyr    Thr    Val    Leu    Ser    Val    Gly    Pro    Gly    Gly    Leu    Arg    Ser    Gly
                             100                          105                           110

Arg    Leu    Pro    Leu    Gln    Pro    Arg    Val    Gln    Leu    Asp    Glu    Arg    Gly    Arg    Gln
                      115                          120                           125

Arg    Gly    Asp    Phe    Ser    Leu    Trp    Leu    Arg    Pro    Ala    Arg    Arg    Ala    Asp    Ala
                      130                          135                           140

-continued

```
Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Arg Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Thr Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Arg Arg Leu Arg
                485                 490                 495

Ala Arg
```

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Asp Gly Tyr Cys
1

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GGAAGATCTT CC                                            1 2

DNA ENCODING FOR A PROTEIN CONTAINING THE EXTRACELLULAR DOMAIN OF LYMPHOCYTE ACTIVATION GENE 3

CROSS-REFERENCE TO RELATED APPLICATIONS

The present application is a divisional of U.S. application Ser. No. 08/416,478, filed Apr. 4, 1995, which is a continuation of U.S. application Ser. No. 07/854,644, filed Sep. 8, 1992, now abandoned, which is the national stage of Ser. No. PCT/FR91/00009, filed Jan. 8, 1991.

The present invention relates to proteins produced by human lymphocytes and, in particular, to a protein expressed at the surface of the latter, DNA sequences coding for these proteins and the pharmaceutical and biological uses of these proteins.

A certain number of protein structures of the cell surface "belong" to the "superfamily" of the immunoglobulins (IgSF). This family of molecules includes the proteins comprising at least one domain with a characteristic folding region called the Ig fold. Several of these molecules have essential functions in immune responses.

In addition to ensuring specific antigen recognition, as do for example the immunoglobulins and the T receptors, they may function as monomorphic ligands critical in cell-cell interactions (for example ICAM, CD4, CD8), receptors for viruses (for example CD4, ICAM) or receptors for the lymphokines (for example IL1-R, IL6-R).

The discovery and characterization of the membrane proteins expressed on the lymphocytes have been facilitated by the development of genetic engineering techniques. By means of various experimental techniques, this methodology makes it possible to characterize the genes coding for the proteins and hence to deduce the peptide sequence from knowledge of the nucleotide sequence of the gene. Other applications of these genetic engineering techniques based on the same experimental principles enable virtually unlimited quantities of the proteins corresponding to the genes which have been discovered to be produced as a consequence of procaryotic or eucaryotic systems of expression.

The inventors have attempted to discover novel genes coding for hitherto undescribed membrane proteins.

The development of the experiments of the inventors has led to the isolation of a novel complementary cDNA designated FDC from natural cytotoxic lymphocytes. This cDNA codes for a protein called LAG-3 (for Lymphocyte Activation Gene-3) which possesses a signal sequence which is thought to be removed to generate the mature protein.

Consequently, the present invention relates to a DNA sequence comprising the nucleotide sequence designated FDC, corresponding to the cDNA sequence represented in the sequence SEQ ID No. 1.

Translation starts at nucleotide 231 and ends at nucleotide 1724.

The present invention also relates to the protein encoded by FDC, namely the protein LAG-3 represented in the sequence ID No.9 (protein sequence 1 to 498).

The first 28 amino acids should constitute a signal sequence which has been removed in the nature protein.

Hence, the present invention relates more particularly to the protein corresponding to the protein sequence 1 to 470 of SEQ ID No. 7.

The mature protein constitutes a membrane protein of type I of 470 amino acids, the theoretical molecular mass of which deduced from the protein structure is 51295 daltons and the isoelectric point is 10.9. It comprises an extracellular region containing about 420 amino acids and a cytoplasmic region containing about 24 amino acids linked by a transmembrane peptide containing about 26 amino acids. The extra-cellular part of the LAG-3 protein corresponds to the amino acids 1 to 420 of the LAG-3 protein described above.

Comparison of the sequence of the LAG-3 gene represented by the cDNA FDC above as well as the exon/intron organisation of the LAG-3 gene with those of other molecules of the Ig/SF type has revealed a close relationship of the LAG-3 protein with the CD4 protein.

It is known that the genes of eucaryotic cells exhibit the phenomenon of polytypy. As a result of this phenomenon, some of the amino acids of the coded protein are sometimes replaced without modification of the activity. The present invention includes the proteins resulting from this phenomenon.

Hence, the present invention relates more generally to a protein having the peptide sequence corresponding to the sequence SEQ ID No. 2, SEQ ID No:7, SEQ ID No:9 and the sequences which differ from it by one or more amino acids and which possess the same activity.

Furthermore, the inventors have found a DNA sequence which is a promoter region for a gene coding for a protein according to the invention. This sequence is that represented in sequence SEQ ID No:3

Consequently, the present invention also relates to this DNA sequence.

The present invention also relates to a DNA sequence comprising the promoter DNA sequence as defined above and a DNA sequence coding for a protein according to the present invention.

In the present invention, the inventors first isolated a FDC complementary DNA by means of the following operations.

culture of lymphocyte cells known as natural cytotoxic cells isolation from these lymphocytes of the messenger RNA bound to the membranes of the intracellular endoplasmic reticulum isolation of the single-stranded complementary DNA from the messenger RNA, then of the double-stranded complementary DNA insertion in a vector such as the bacteriophage lambda gt10 preparation of a single-stranded DNA probe from the messenger RNA of the cells and purification by means of a subtraction-hybridization technique so as to select the copies of the RNAs present in the natural cytotoxic lymphocyte cells and absent from other transformed hematopoietic cells.

selection of the complementary DNAs inserted into the vector which react with the probe transfer of the DNA selected into a plasmid vector in order to amplify, purify and sequence it.

The protein sequence according to the invention was obtained by:

translation of the nucleotide sequence of the FDC cDNA.

The existence of this protein in the natural state on T cells was demonstrated by:

preparation of sera directed against a synthetic peptide representing a region probably exposed toward the exterior of the product of translation of the FDC cDNA which has a protein structure in the form of a loop, immunoprecipitation of the LAG-3 protein by anti-peptide hetero-antibodies.

The proteins according to the invention may also be obtained by other methods of purification of membrane proteins or by classical peptide synthesis or also by application of genetic engineering techniques comprising the insertion of a DNA sequence coding for a protein according to the invention into an expression vector such as a plasmid and the transformation of cells with this expression vector and the culture of these cells.

Hence, the present invention also relates to plasmids and expression vectors comprising a DNA sequence coding for a protein according to the invention as well as hosts transformed with this vector.

The present invention also relates to a therapeutic composition containing as active ingredient a protein according to the invention or a part of this protein, in particular the soluble part corresponding to the extracellular region of the protein extending from amino acid 1 to amino acid 420 of the protein sequence-previously described or a part of this extracellular region and, in particular, all or part of at least one of the four extracellular domains of the immunoglobulin type of the LAG-3 protein (sequences 1 to 142, 143 to 232, 233 to 342 and 343 to 413). The part of the protein may also be constituted by all or part of the cytoplasmic region (sequence 450 to 470). The extracellular part may, in particular, be the sequence represented in the sequence SEQ ID No. 3.

This therapeutic composition is active in the treatment of certain diseases implicating the immune system in which the binding of the ligand(s) of the LAG-3 protein to this protein causes the transmission of signals into the interior of the cell, or modifications of cellular interactions.

In this case, the composition according to the invention may act by binding the ligand(s) of the membrane protein LAG-3, thus preventing the detrimental binding of this ligand or these ligands to the LAG-3 protein by a phenomenon of competitive inhibition.

The present invention also relates to monoclonal antibodies directed against a protein according to the invention or an immunogenic sequence of such a protein, in particular a peptide sequence comprising the sequence represented in SEQ No. 3.

The present invention also relates to hybridomas producing such monoclonal antibodies.

The present invention also includes the fragments and derivatives of the monoclonal antibodies according to the invention which react with defined regions of the LAG-3 protein. Such fragments are, in particular, the F(ab')$_2$ fragments which may be obtained by enzymatic cleavage of the antibody molecules with pepsin, the Fab' fragments which may be obtained by reduction of the disulfide bridges of the F(ab')$_2$ fragments and the Fab fragments which may be obtained by enzymatic cleavage of the antibody molecules with papain in the presence of a reducing agent. These fragments as well as Fv fragments may also be obtained by genetic engineering.

The monoclonal antibody derivatives are, for example, antibodies or fragments of these antibodies to which markers such as a radioisotope are linked. The monoclonal antibody derivatives are also antibodies of fragments of these antibodies to which therapeutically active molecules, in particular cytotoxic substances, are linked.

Furthermore, the monoclonal antibodies or the soluble fractions of the LAG-3 protein and, in particular, all or part of at least one of the four extracellular domains of the immunoglobulin type of the LAG-3 protein (sequences 1 to 142, 143 to 232, 233 to 342 and 342 to 413) or the cytoplasmic region (sequences 450 to 470) of this protein may be used in the treatment of human diseases due to infection by viruses of the HIV type.

These same products may be used in the treatment of human diseases in which a pathophysiological mechanism causes intercellular adhesion interactions between a ligand and LAG-3 (in particular with the first and/or second external domain of LAG-3) such as, for example, the autoimmune diseases.

They may also be used in the treatment of the human diseases caused by viruses binding specifically to the LAG-3 molecule and, in particular, to the first, NH$_2$-terminal external domain.

The present invention also relates to a dosing or identification method for the proteins according to the invention which comprises the use of the monoclonal antibodies according to the invention.

For this purpose it is possible to use, in the case in which a part of the LAG-3 protein is soluble in the native state, a radio-immunological method of the RIA type or the IRMA type (technique of the sandwich type using a cold antigen and competition between a cold antibody and a labelled antibody) or an immuno-enzymatic method of the ELISA type or the IEMA type (technique of the sandwich type).

In order to identify the LAG-3 protein bound to the membrane, it is possible to use methods such as direct immunofluorescence (using anti-LAG-3 antibodies labelled with a fluorescent substance) or indirect immunofluorescent (by using a labelled anti-Ig mouse immunoglobulin in the case in which the anti-LAG-3 antibodies have been produced in this species).

The monoclonal antibodies directed against the proteins according to the invention or fractions of them may be prepared according to a standard method. For this purpose, the protein fractions may be coupled if necessary to an immunogenic agent such as tetanus toxoid by means of a coupling agent such as glutaraldehyde.

BRIEF DESCRIPTION OF THE DRAWINGS

A more detailed description will be given hereafter of the isolation of the FDC cDNA and the LAG-3 gene coding for the protein by referring to the appended figures in which:

FIG. 5 presents the alignment of the domains 1 and 2 (Corresponding to amino acid residues 119 to 264 of SEQ ID NO:9) with the domains 3 and 4 (corresponding to amino acid residues 304 to 435 of SEQ ID NO:9 of the LAG-3 protein;

FIG. 6 presents the alignment of the peptide sequences of LAG-3 (SEQ ID NO:9) and the CD4 (SEQ ID NO:8) protein of the rat;

Figure 1:
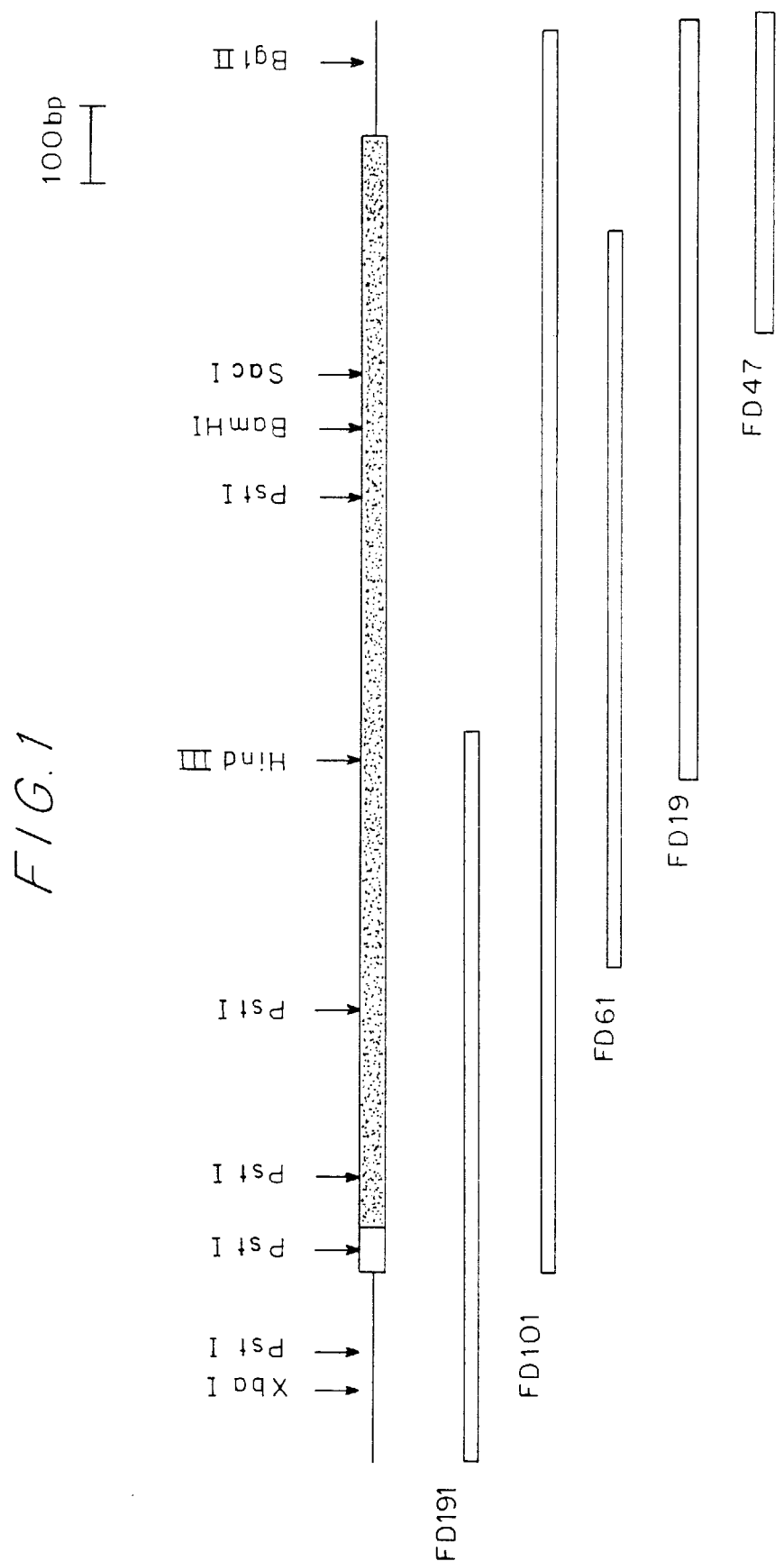
FIG. 1 presents the restriction map of the FDC cDNA and the clones of cDNA which have enabled the sequence of the FDC clone to be determined.

I—Culture and Preparation of the mRNA Linked to the Membranes of the Endoplasmic Reticulum The isolation and the characteristics of the fetal clone, F55IIIF5 (phenotype CD3$^-$ CD2$^+$) have been previously described by Nowill et al (1).

The mass culture was carried out in the presence of recombinant interleukin-2 and the supernatant of lymphocyte-conditioned medium on a feeder substratum of allogenic irradiated mononucleated blood cells and a cell line transformed by the EBV virus (called LAZ 388) on V-bottomed 96-well plates. 3000 cells were placed in each well at day 0. The pooling of 200 plates with 3×10$^6$ cells per ml at day 12 gave a harvest of 6×10$^9$ cells.

The preparation of the cytoplasmic RNAs, the RNAs bound to the membranes of the endoplasmic reticulum and the mRNAs was performed by introducing some modifications to the methods described by Maniatis (2), Mechler (3) and Aviv (4). Thus, 4×10$^9$ F55IIIE5 cells were loaded onto sucrose gradients after hypotonic shock and mechanical grinding according to the method described by Mechler. The cytoplasmic RNAs borne by the ribosomes bound to the membranes of the endoplasmic reticulum were purified between sucrose gradients. This makes it possible to work subsequently with mRNAs which have a signal sequence and which consequently codes for proteins borne by the membrane or secreted into the internal part of the ergastoplasm (and towards the exterior of the cell). This method of isolation of RNA of the so-called MB (membrane-bound) type makes it possible to remove rightaway about 90% of the transcribed genes which code for intracellular proteins incapable of being secreted towards the exterior or transported towards the membrane and, consequently, of no interest in the context of the invention. In addition to the isolation of the MB-F55IIIE5 mRNA which serves as substrate for the construction of the library, on the one hand, and the preparation of the probe, on the other, the methods of purification described by Aviv (4), Maniatis (2) and Triebel (5) made possible the isolation of RNAs of the various clones and cell lines which are used and mRNAs of Jurkat, U937, Laz388 and K562 cells (about 10$^9$ cells of each line) which are used to subtract the probe.

These methods comprise:

A—Preparation of the Cytoplasmic RNA 1 ml of lysis buffer (50 mM Tris HCl, 62.5 mM EDTA, 0.4% Triton X-100, 2.5M LiCl) is added to a vial containing 20 to 30×10$^6$ cells as a dry pellet. After gentle dissolution of the pellet, the lysis buffer is transferred to cold Eppendorf tubes containing 50 µl of 10% NP40.

After 5 mn on ice, the tubes are centrifuged for 1 min at 8000 rev/min. The supernatant (RNA) is removed and introduced into Falcon tubes containing 1 ml of phenol, 1 ml of CHCl$_3$, 1 ml of STE 2% SDS (150 mM NaCl, 10 mM Tris, 1 mM MgCl$_2$, 2% SDS). The tubes are centrifuged for 10 min. at 5000 rev/min. The upper phase is removed, 1 ml of phenol and 1 ml of chloroform are added. After centrifugation for 5 min. at 5000 rev/min., the upper phase is removed. 100 µl of 0.2 M EDTA, 200 µl of 3M NaAc and 5 ml of ethanol are added. The mixture is left at −20° C. overnight before being centrifuged for 30 min at 10000 rev/min. The pellet is dried. It is taken up in 400 µl of cold 0.3M NaAc. 1 ml of ethanol is added to the Falcon tube. The ethanol is transferred to the Eppendorf, the mixture is left for 1 h at −20° C. The mixture is centrifuged for 10 min at 13K, the alcohol is aspirated and the pellet is dried. 30 µl of water are added. The solution is centrifuged and frozen immediately at −80° C. The degradation and the amount are checked by placing 1 µl on a denaturing gel (1% agarose in TBE buffer (Tris, Base, EDTA), pH 8.5, autoclaved (BET 1 µg/ml).

B—Preparation of the Messenger RNA Bound to the Membranes of the Endoplasmic Reticulum The cells are taken up in ice-cold hypotonic RSB buffer (10 mM KCl, 1.5 mM MgCl$_2$, 10 mM Tris-HCl, pH 7.4) treated beforehand with 0.1% DEPC at 10$^8$ cells/ml. They are left on ice for 5 min. The cells are ruptured mechanically by means of 10 strokes of a Dounce homogenizer (type B). The homogenate is centrifuged at 1000 g for 2 min in order to sediment the nuclei. The supernatant or "cytoplasmic extract" is then used for the separation of free ribosomes/ membrane extracts. 0.7 ml of cytoplasmic extract is mixed with 3.2 ml of 2.5M sucrose TK buffer (0.05M Tris-HCl, pH 7.4, 0.15M KCl, 0.005M MgCl$_2$), then this mixture is layered onto 2 ml of 2.5M sucrose TK. 8 ml of 2.05M sucrose TK are added, followed by 4 ml of 1.3M sucrose TK. The gradients are centrifuged at 4° C. for 5 h in a swinging rotor of the Spinco SW28 type at 25000 rev/min. The tubes are punctured with a needle at the interphase between the 2.05M and the 1.3M sucrose gradients. One volume equal to TE 10:1 (10 mM Tris HCl, 1 mM EDTA) is added. An extraction is made with phenol, then with a phenol-chloroform mixture. Precipitation is effected with ¹⁄₁₀ of 3M NaAc and 2.5 vol. of ethanol.

For the isolation of the poly (A)$^+$ RNA a column of oligo (dT)-cellulose is used containing 1.2 ml of gel equilibrated with the loading buffer:20 mM Tris-HCl (pH 7.6), 0.5M NaCl, 1 mM EDTA supplemented with SDS. The column is washed with H$_2$O, a 0.1M NaOH solution and 5 mM EDTA and water. It is then washed with 5 volumes of loading buffer. The RNA is dissolved in water and heated at 65° C. for 5 min. An identical volume of loading buffer is added twice. The temperature is allowed to equilibrate. The effluent is collected. It is heated at 65° C. and the sequence is repeated. The column is washed with 5 to 10 volumes of loading buffer, then with 4 volumes of loading buffer −0.1M NaCl. The poly(A)$^+$ is eluted with 2–3 volumes of 10 mM Tris-HCl (pH 7.5), 1 mM EDTA, 0.05% SDS.

3M sodium acetate (pH 5.2) is added at ¹⁄₁₀. Precipitation is effected with 2.2 vol. of ethanol.

II—Construction of the cDNA Library

The in vitro preparation of the single-stranded complementary DNA starting from the messenger RNA bound to the membranes of the endoplasmic reticulum of the F55IIIE5 cell, followed by the double-stranded complementary DNA is carried out according to the techniques described by Gubler et al (6).

After protection of the internal EcoRI sites by the EcoRI methylase and size selection on an agarose gel at low temperature permitting the selection of fragments of size larger than 500 bp, the double-stranded cDNAs were cloned into the EcoRI site of the phage Lambda gt10 with the aid of the EcoRI linker.

The in vitro packaging of the recombinant Lambda gt10 phages was performed using a commercial cloning kit (Amersham Corp. Arlington Heights, Ill.

After plating on *E. coli* C 600 Hfl$^+$, 6×10$^4$ recombinant phages are obtained.

III—Preparation of the Complementary DNA Probe

The preparation of the single-stranded complementary DNA probe is carried out by subtraction by means of two cycles of hybridization on an excess of messenger RNA of the cells said "to be eliminated" (Jurkat, Laz 388, U937, K562), followed by passage through hydroxyapatite columns which enables the double-stranded cDNA-mRNA complex to be separated. After 2 hybridization cycles and 2 passages through the column about 6–7% of the radioactivity remain, i.e. that about 7% of the F55IIIE5 material called MB ("membrane-bound") does not exist in the Jurkat, K562, U937 and Laz 388 cells. It is this material which serves as probe for the detection of the corresponding cDNAs in the MB-F55IIIE5 library. This technique makes use of the subtraction-hybridization conditions described by Davis et al (7).

Preparation of the subtracted probe/MB-FSSI-IIES-mRNA of Jurkat, K562, Laz 388, U937/

Starting from 5 µg of MB-F55IIIE5 mRNA, a single-stranded cDNA probe is prepared labelled with $^{32}$P-dCTP (specific activity 800 Ci/mmol$^{-1}$) in a volume of 50 µl.

After incubation for 2 h at 42° C. with the reverse transcriptase enzyme, 5 µl of 0.2M EDTA are added, followed by 50 µl of 0.2N NaOH. The mixture is incubated at 65° C. for 1 h. 60 µl of 1N HCl and 30 µl of 2M Tris-HCl (pH 8) are added. ⅒th vol. of 3M NaAc is added. 7 µl of mRNA of each of the 4 tumor lines are added in order to precipitate the probe, then 2.5 vol. of ethanol are added.

The mixture is left for 1 h at −20° C. before being centrifuged, washed with 70% ethanol and dried. The precipitate is taken up in 7.5 µl of H$_2$O, and 7.5 µl of 0.5M NaH$_2$PO$_4$, pH 7, 1 mM EDTA, 0.25% SDS are added. The solution is incubated in the incubator at 68° C. for 20 hours.

The solution is diluted with 1 ml of 0.12M NaH$_2$PO$_4$, 0.1% SDS. It is loaded onto a hydroxyapatite column equilibrated with the same buffer at 60° C. The effluent (single-stranded material) is concentrated using sec.butanol and passed through a G-50 column in order to remove the phosphate buffer. 7 µg of mRNA of each of the lines are added again and the hybridization and passage through the column are repeated. After these 2 passages, 7% of the starting amount of radioactivity are recovered.

IV—Isolation and Characterization of the cDNA Clones

The previously constructed cDNA library (2×10$^4$ recombinant phages) is inoculated into E. coli C600/Hfl. The screening is performed in accordance with the usual techniques using nylon filters as described by Huynh (8).

Hybridization with the probe previously obtained is carried out at 42° C. with prehybridization with a hybridization solution of the Southern type and addition of 5×10$^6$ cpm/ml of the single-stranded MB-F55IIIE5 subtracted probe.

After two subtraction-hybridization cycles, 120 positive lambda gt10 phages are identified out of the 2×10$^4$ recombinants.

The plating of the positive phages, the purification of the corresponding DNAs, the purification of the complementary DNAs in the form of fragments by excision from an agarose electrophoresis gel with a low gelling point were carried out according to the method described by Maniatis (2) and Huynh (8).

The ligation of the longest cDNAs in the plasmid vector pBS digested by the EcoRI endonuclease and treated with the alkaline phosphatase calf intestine, the transformation of competent JM 109 bacteria and the screening of the recombinants by a double selection system (ampicillin+X-gal/IPTG) were carried out according to the methods of genetic engineering conventionally used.

The purification and the preparation on a large scale of the recombinant complementary DNAs cloned in pBS were carried out by using the method of purification on a cesium chloride gradient described by Maniatis (2).

A cDNA clone was isolated which has been designated FD47 and which consists of 400 bp and hybridizes with the probe obtained by subtraction-hybridization. This clone was selected, on the one hand, because it hybridizes with a transcript of 2 kb constantly found in the F55IIIE5 cells but not in the Jurkat, Laz 388,K 562 and U 937 cells in the "Northern blot" techniques and, on the other, because it shows no homology with any of the known sequences of the data bank entitled "Genebank". The FD47 clone contains a nucleotide region capable of coding for a hydrophobic transmembrane region.

V—Isolation and Structure of a Full-length DNA.

Among the 120 positive lambda gt10 phages obtained after subtraction-hybridization, no other phage was observed to cross-hybridize with FD47.

In order to establish the sequence of cDNA called FDC, three new cDNA libraries are constructed starting either from oligo-dT primers, or a hexamer of random sequence or a specific primer consisting of the nucleotides 704 to 688 of FDC. Furthermore, a single-stranded RNA probe labelled with $^{32}$P is constructed starting from FD47 by in vitro transcription from the pBS plasmid using the T7 polymerase in the presence of $^{32}$P-UTP (800 Ci.mmole$^{-1}$) according to the method described by Triebel (5). The three libraries are constructed from the messenger RNA derived from CD3$^+$ clones bearing the γ and δ of the T receptor and which transcribe a LAG-3 message in considerable quantities when their RNA is tested with the FD47 probe.

The FD47 probe is used to screen the first cDNA library in order to obtain the clone FD19.

In the same manner as previously described, a 0.3 kb Bam HI—Hind III genomic fragment comprising the most 5' part of the IV exon is labelled using as primer a random hexamer and it is used to screen the second library to obtain the clones FD61 and FD101, and the third library in order to obtain a cDNA containing the almost full-length 5' end, called FD191.

The sequences of the clones FD47 and FD19 were determined directly in the pBS vector by the method of Sanger (9) using a universal M13 primer or a reverse M13 primer and the modified T7 polymerase.

The sequences of FD61, FD101 and FD191 were determined from single-stranded DNA after cloning in the vector M13mpl8.

After different overlapping cycles of hybridization ("DNA walking") by using the 3 cDNA libraries obtained using different primers, cDNA clones are thus isolated, the sequences of which overlap and which cover a total of 1.8 kb.

The set of the total nucleotide sequences of these cDNAs called "FDC sequence" consisting of 1871 bp indicates that the messenger RNA of the LAG-3 gene has a long and open reading frame and codes for a protein of 498 amino acids, the peptide sequence of which is obtained by deduction from the nucleotide sequence of the cDNA.

The FDC cDNA itself was obtained by ligation of the 2 complementary EcoRI-HindIII fragments, one covering the 5' part of the FD191 clone, the other covering the 3' part of the FD19 clone, thus producing a clone covering the entire known sequence, as illustrated in FIG. 1.

VI—Isolation and Structure of the LAG-3 Gene

A/ Molecular cloning of the LAG-3 gene

Genomic DNA clones are isolated from the LY67 library made from DNA of a human B cell line transformed by EBV, partially digested with Mbo-I and inserted into the phage lambda 2001 as described by Dariavach (10). The FD47 insertion segment is labelled by means of the hexamer random priming method described by Feinberg (11) and used to screen $2 \times 10^5$ plaques of the human genomic DNA library. Nine positive plaques (GD1 to GD9) are isolated and the phage DNAs are characterized by restriction mapping using the FD19 probe containing half of the region coding for the protein and the untranslated 3' region.

Figures 2, 3:
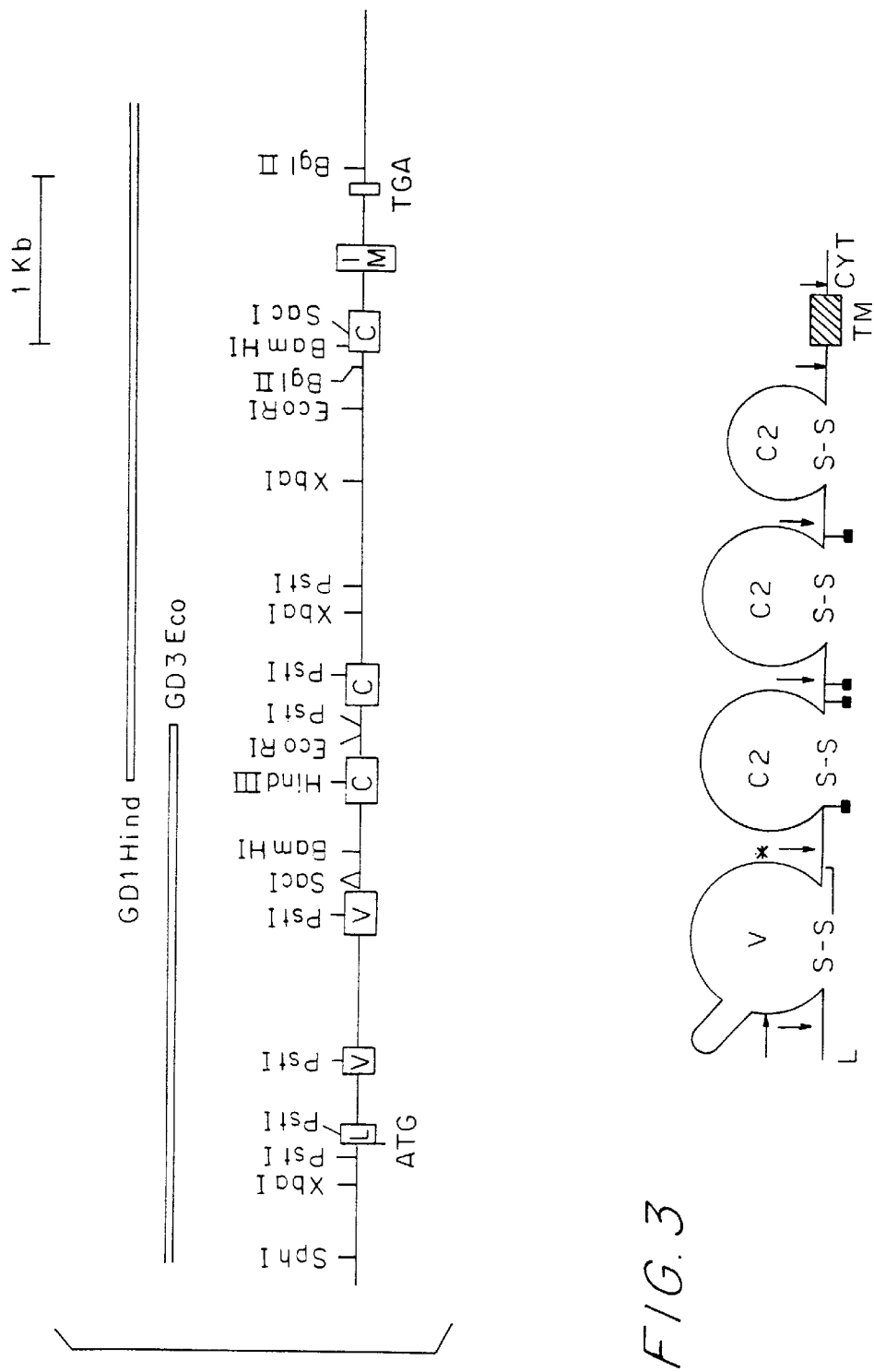
FIG. 2 presents the restriction map and the distribution of exons and introns in the LAG-3 gene.
FIG. 3 is a schematic representation of the LAG-3 protein.

Two overlapping DNA fragments of 16.4 kb (EcoRI) and 11.5 kb (Hind III) are obtained and subcloned in the plasmid pUN121 to give the clones GD3Eco and GD1Hind, as shown in FIG. 2.

Detailed restriction maps of these subclones are constructed and compared with the restriction map of the FDC sequence shown in FIG. 1.

Many fragments are obtained on an agarose gel with a low gelling point and are subcloned in the bacteriophages M13mp18 or M13mp19.

The sequences of these fragments are determined from single-stranded DNA using the dideoxy chain termination procedure described. Oligonucleotides containing 17 bases, the sequences of which are obtained either from the cDNA of FD19 or from the sequence of the 5' flanking region of the LAG-3 gene are synthesized and used for sequencing.

B—Structure of the LAG-3 Gene

FIG. 2 illustrates the exon-intron organisation of the human LAG-3 gene. The map was constructed after single and double digestion by endonucleases of the $GD_2$ and $GD_3$ clones obtained from lambda 2001 and their subclones $GD_3$ Eco and $GD_1$ Hind. The untranslated regions are represented by a fine line.

The LAG-3 gene spends approximately 6.6 kb and is divided into 8 exons, the first nucleotides of which are located at positions 1, 289, 437, 742, 1012, 1288, 1531 and 1662 of the DNA sequence previously described.

The so-called promoter region at the 5' end of the LAG-3 gene whose sequence was previously described has been studied and enabled the following observations to be made:

- no characteristic TATA box is found upstream from the 239-bp untranslated 5' region;
- the nucleotide sequence contains a CCAAT box in reverse (i.e. ATTGG) at position −662 from the ATG sequence signalling the initiation of translation.

The CCAAT box is known to be crucial in many promoters and may function in the reverse orientation.

- an Spl binding site containing the typical GGGCGG core hexanucleotide is also located at position −339 from the translation initiation site.

In order to estimate the number of copies of the LAG-3 gene in the human genome, the DNA of the K562 tumor cell line and of the polyclonal IL-2-dependent T and NK cell lines are digested with EcoRI, Hind III, Bam HI or XbaI. Southern Blot hybridizations are performed using the FDC probe (1871 bp), constructed by fusion of the 5' EcoRI/Hind III fragment of the FD191 clone with the 3' Hind III/EcoRI fragment of the FD19 clone. 3 fragments of 2, 8.2 and 10 kb are obtained with EcoRI, 2 fragments of 5.7 and 9.5 kb with Hind III, 3 fragments of 2.8, 4 and 13 kb with Bam HI and 3 fragments of 3, 4 and 6 kb with XbaI.

These results indicate that a single copy of the LAG-3 gene is present in the human haploid genome. Furthermore, the analysis of the T, B and NK cells using the same technique shows that there is no rearrangement of the LAG-3 gene in the cells during the differentiation of the lymphocytes.

VII—Expression of the LAG-3 Gene

The 1004 bp fragment inserted in the FD19 clone was used as probe to analyse the cellular distribution of the expression and the regulation of the expression of the LAG-3 gene.

The results of the RNA "blotting" clearly show that the subtraction-hybridization procedures used in the first screening of the F55IIIE5 sub-library were performed successfully with respect to the isolation of the FD19 clone of the cDNA library in the sense that no LAG-3 transcript is expressed in the transformed cell lines of T, B and myeloid origin (in particular Jurkat, Laz 388,K 562, U 937).

Assays were performed on other lines of transformed T cells including CEM and MOLT-4 and none was found to express LAG-3. The same was true for the peripheral circulating monocytes.

A selection of polyclonal lines or clones of normal T and NK cells placed in culture was also tested. In the latter case, LAG-3 messenger RNA was detected as a single species of about 2 kb in all of the lines studied:3 $CD3^-$ lines (F55 III E5, SIIH4, SIII G5), 4 $CD3^+$ TCR /$\beta^+$ lines ($CD4^+$: SIF8 and F55IIIG5 and one $CD3^+$ $TCR\tau/\delta^+$ line (the clone $TCR\delta1^+$ $Ti\tau A^+$ BK).

However, messenger RNA was not detected in fresh, purified T cells nor in peripheral macrophages nor in resting lymphocytes, within the limits of detection usually accepted for this technique.

The expression of the LAG-3 gene has also been studied in the nervous tissues of neuroectodermal origin and no messenger RNA was detected in either the neuroblastoma cell lines in culture or in fresh cerebral tissue.

The LAG-3 gene is only expressed in the T and NK cells after activation.

The expression of the LAG-3 gene is maximal 3 to 4 days after activation of the blood lymphocytes by phytohemagglutinin. Hence, the protein corresponds to what is appropriately called an activation antigen.

VIII—Structure of the LAG-3 Protein

Figure 4:
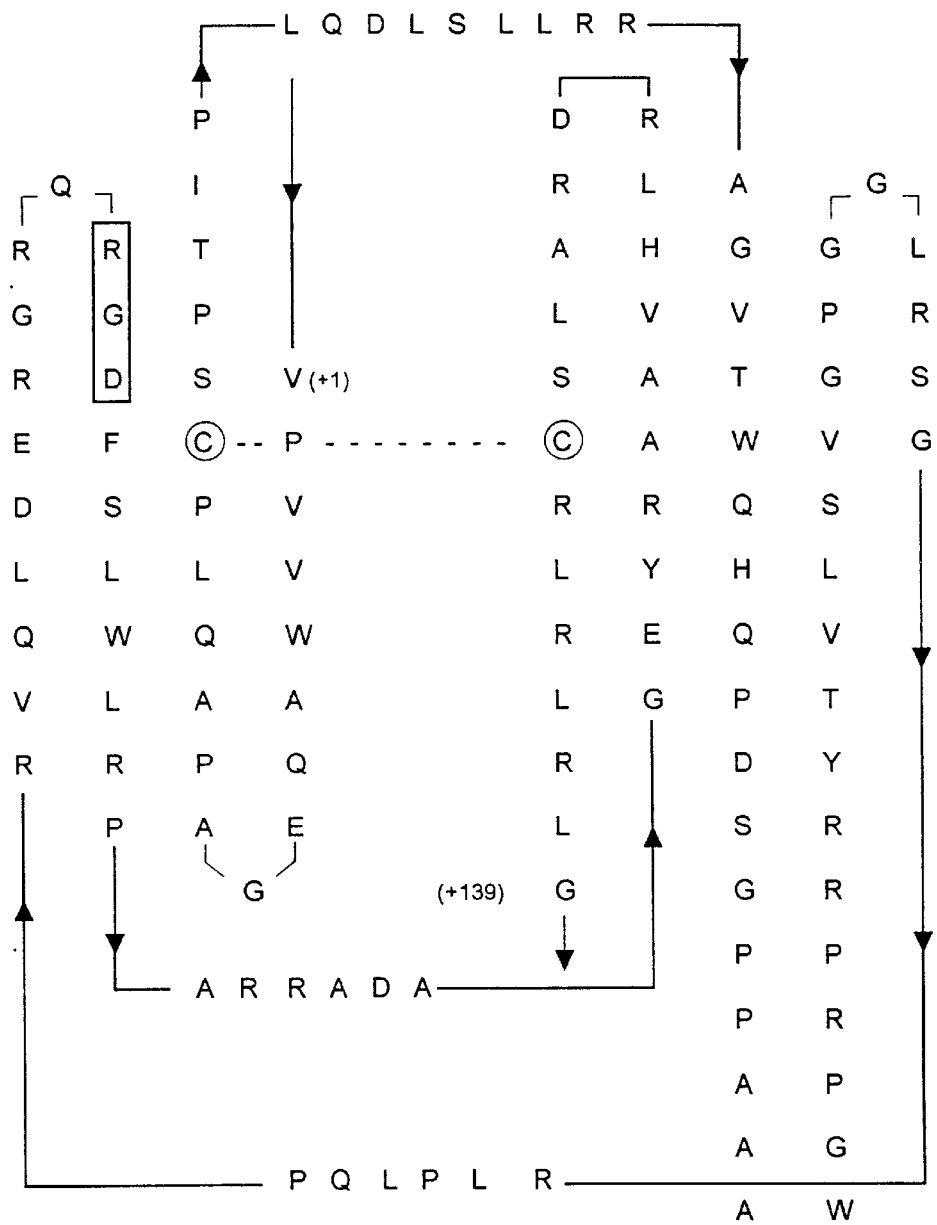
FIG. 4 presents a model of the domain 1 of the LAG-3 protein corresponding to amino acid residues 1 to 139 of SEQ ID NO:7.

The characteristics of the LAG-3 protein, shown in FIGS. 3, 4 and 6, have been deduced from the structure of the gene and from the analysis of its translation product. It appears to be a type I membrane protein containing 498 amino acids.

As shown in FIG. 3, the domains are designated by L (leader domain), V (V domain of the immunoglobulin type), $C_2$ ($C_2$ domain of the immunoglobulin type) (19), TM (transmembrane) and CYT (cytoplasmic). The position of the introns is indicated by arrows. The N-glycosylation sites and the RGD sequence (cell attachment sites) are also indicated.

The mature protein comprises 470 amino acids with a theoretical molecular mass of 51295 daltons and an isoelectric point of 10.9 based on protein structure analysis. It contains a leader peptide L (28 amino acids) encoded by the exons I (19 amino acids) and II (9 amino acids out of 50). The extracellular region is encoded by the exons II (41 amino acids out of 50), III (101 amino acids), IV (90 amino acids), V (92 amino acids) and VI (81 amino acids), the transmembrane (TM) region by the exon VII (44 amino acids) and the cytoplasmic region including strongly charged amino acids by the exon VIII (21 amino acids). The extracellular region contains 8 cysteine residues and 4 potential N-glycosylation sites (Asn-X-Ser, Thr).

FIG. 4 presents a model of domain 1 of the LAG-3 protein. The sequence of the first domain of the Ig type (amino acids +1 to +139) is represented according to the model used by Amzel and Poljak (12). The disulfide bridge is shown and the RGD sequence is boxed in.

The peptide segment encoded by the exons II and III corresponds to a V type IgSF domain as described by Williams (13) including the β-strands A, B, C, C', C", D, E, F and G shown in FIG. 6, possessing two unusual features.

Firstly, this V-type domain includes an extra loop of approximately 30 amino acids encoded by the first part of the exon III. This loop shown in FIG. 4 joins the β-strand C to the β-strand C' and contains, in particular, ten proline residues. It seems that such an insertion might be compatible with a IgSF-type fold to the extent that it does not cause rupture of the central core of the fold that is considered to consist of the β-strands A, B, E and G, F, C as described by Lesk (14).

This extra loop acts as immunogen since it is probably exposed at the outside of the molecule and consequently is exposed to recognition by antibodies.

As a general rule the differences in the V-type and C-type domains appear in the middle of the Ig-type fold at this site, i.e. in the region of the C β-strand.

Furthermore, the insertion of a peptide structure encoded by a supplementary exon (15), forming an additional mini-loop, has been described in domain 4 of the N-CAM molecule.

The second unusual feature is that the cysteine downstream from domain 1 seems to be located in the β-strand G rather than in the βstrand F (residue 121), as is almost invariably the case. The sequence Asp-Gly-Tyr-Cys (SEQ ID NO:10) is located very characteristically in the β-strand F and is found here, except that a Ala residue replaces the Cys residue (FIG. 4). It seems possible that a disulfide bridge may be formed and, for example, it should be noted that an unusual disulfide bridge of a different kind has been oberved in the V-type domain of the ∝ chain of CD8 as described by Kirszbaum (16).

A Arg-Gly-Asp (RGD) sequence is found in the β-strand E (FIG. 4). This sequence is known to represent a potential adhesiotope as described by Ruoslahti (17) but it has not been established whether it forms the core of an essential binding site since, in this position, such a sequence would probably be located within the IgSF-type fold.

The exons IV, V and VI code for IgSF-related domains as described by Williams (13) with 51, 50 and 42 amino acids, respectively, between the two conserved cysteine residues. These three domains possess C-type folds and show sequence patterns characteristic of the C2-type domain (13). They have been compared with sequences of the C2-type domain with the aid of the ALIGN program according to the method described by Dayhoff (18) and Williams (19). Of 57 sequences examined, scores greater than 3SD (standard deviations) were obtained 32, 41 and 11 times for domains 2, 3 and 4, respectively. Domain 4 belongs to the truncated C2-type domain in the sense that it does not possess the β-strand D.

The domains 1 and 2 of LAG-3 were aligned and compared by eye with the domains 3 and 4, taking into account identities and structural considerations.

FIG. 5 shows the internal homology of LAG-3.

The amino acid sequences of domain 1 (starting from position 91 in FIG. 5 (and in accordance with the numbering in FIG. 5) after the extra loop) and domain 2 were aligned with the corresponding positions in domains 3 and 4. The identities are indicated by (*) and the similarities by (.).

Since domain 1 contains a sequence forming an extra loop, the alignment was begun at amino acid 91 in this domain and at amino acid 276 in domain 3 of FIG. 5. Out of 129 possible matches between residues, 34 identities, 35 similarities and 9 breaks were observed (alignment score greater than +8.5 SD). Moreover, in the β-strand F of domains 2 and 4, there is a WxC sequence which is most unusual at this position where the sequence Y or FxC is usually found, as described by Williams (13). Taken together, these results suggest that LAG-3 has evolved by gene duplication from a pre-existing two-domain structure resembling that of an Ig L chain.

The sequences of LAG-3 and CD4 of the rat have also been aligned, as is shown in FIG. 6. The dotted lines above the sequences show the positions of the β-strand in the four IgSF-type domains. The leader sequence L and the transmembrane sequence (TM) are shown by a continuous line above the sequence. The position of the introns is shown by arrows above the sequence (for LAG-3) and below the sequence (for CD4) as described by Maddon (20) for human CD4. Two large gaps are inserted corresponding to the sequence of the extra loop in domain 1 of LAG-3 and in order to account for the fact that domain 3 of CD4 is a V-type domain, whereas domain V of LAG-3 is a C2-type domain. The fragments of similarity comprise the start of domain 1 (9 identities and 10 similarities out of 17 possible matches), and the very unusual sequence WxC in domains 2 and 4 of LAG-3, which are also present at the corresponding positions in CD4. This sequence pattern is not found in an equivalent position in any other IgSF-type domain. Overall, there are 87 identities and 82 similarities out of 338 aligned residues (19 sequence breaks) when the extra-cellular regions of LAG-3 and CD4 of the rat are compared. One of the principal features of LAG-3 is, consequently, its relationship to CD4.

Figure 7:
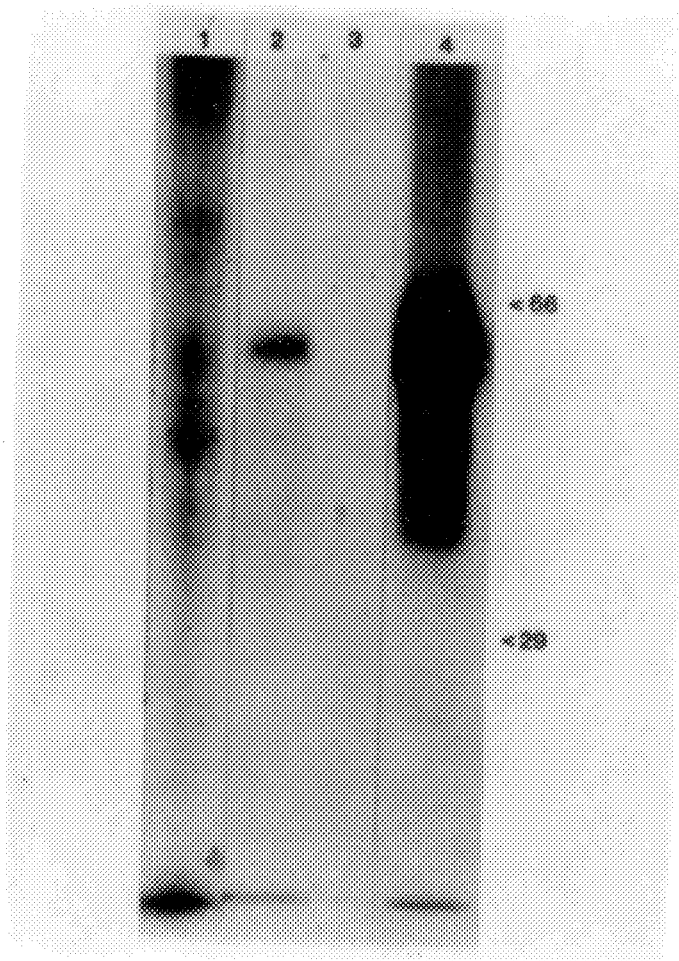
FIG. 7 presents the result of an immunoprecipitation of membrane proteins of PHA-blasts.
Figure 8:
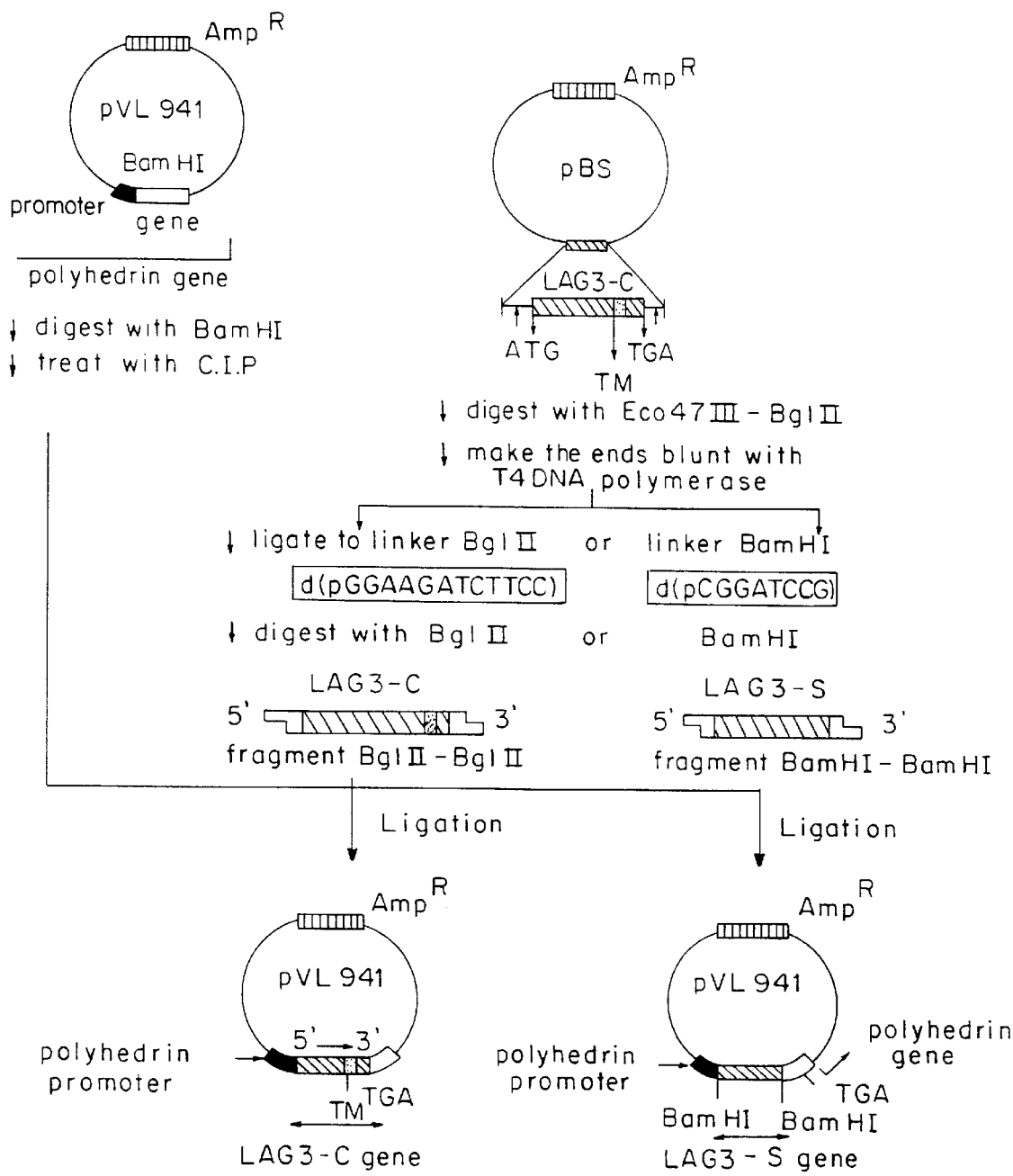
FIG. 8 is a schema for the preparation of a transfer vector (baculovirus system) where linker BglII corresponds to SEQ ID NO:11.

As in the LAG-3 structure known fragments having internal sequence homologies have been found in the CD4 molecule between domains 1 and 3 as well as between domains 2 and 4. More generally, the exon/intron organisation of LAG-3 and CD4 is very similar: both genes comprise an intron within the first IgSF-type domain and the position of the introns (shown by arrows in FIG. 7) in LAG-3 is very similar to that of CD4.

It has been suggested that CD4 has evolved by gene duplication from a pre-existing structure with 2 IgSF-type domains. The present discovery strengthens this hypothesis and the inventors suggest, on the basis of similarities of sequence and exon/intron organisation, that CD4 and LAG-3 have thus shared a common 4-domain ancestor.

The LAG-3 protein may thus be expected to function as do many other molecules of the superfamily of the Ig type as ligand for a soluble protein or for a membrane protein. The known examples include proteins whose expression is positively regulated by cell activation such as ICAM-1, known to be involved in cell-cell interactions, or IL1-R and IL6-R which function as receptors for growth factors.

In view of the fact that the LAG-3 protein is expressed in substantial amounts on activated lymphocytes (probably more than 5000 sites per cell given the limits of detection of indirect techniques of immunofluorescence with a rabbit anti-serum in flow cytometry) and taking into account its homology with CD4, the very likely function of LAG-3 is one of intercellular adhesion. The characterization of the receptor-ligand couples (for example ICAM-1/LFA-1 or CD4/MHC, class II) in this domain is in progress. The CD4 molecule has been crystallized and its atomic structure deduced by X-ray analysis (Ryu (22) Wang (23)). The binding sites for anti-CD4 antibodies, binding sites for the gp120protein of HIV (AIDS virus) and the binding sites for molecules of class II of the major histocompatibility complex (MHC) have been studied and it has become clear that the first $NH_2$-terminal domain (domain 1) is the most important for the functional activity of CD4. It has been shown that soluble CD4 molecules obtained by deletion of the transmembrane and cytoplasmic parts of the natural CD4 molecule either alone or coupled to constant regions of immunoglobulins (creation of a CD4 immunoadhesin (Byrn 24)) are capable of binding the gp120protein and of preventing the dissemination of infection by HIV. Similarly, with respect to the ICAM-1 molecule, it has been shown that the first $NH_2$-terminal domain (domain 1) contains binding sites for LFA-1 and attachment sites for the rhinoviruses (Staunton (25)). Two therapeutic applications which follow from knowledge of the structure of ICAM-1 have been described. The expression of ICAM-1 is considerably enhanced at the surface of the bronchial epithelium during asthmatic disease and in a model of a cynomolgus monkey made asthmatic, it is possible to reduce the infiltration of the bronchi by eosinophil granulocytes and to improve the clinical state by intravenous injection of anti-ICAM antibodies (Wegner (26)). In respect to the utilization of a recombinant molecule made soluble by deletion of the transmembrane and cytoplasmic domains, it has been shown that the soluble ICAM-1 molecule inhibits the infection of human cells by rhinoviruses by blocking the attachment of the virus to the natural ICAM-1 molecule at the surface of the cells by competition (Marlin (27)).

In view of the structural analogies with CD4, it is thus possible that LAG-3 may be a site of entry for a virus. As regards the HIV or related viruses, one of the possible attachment sites may consist (by analogy with CD4) in this case of all or part of the following amino acid sequence including, in particular, the β-strand C" of domain V: Gly Leu Arg Ser Gly Arg Leu Pro Leu Gln Pro Arg Val Gln Leu Asp Glu Arg (corresponding to the amino acids 80 to 97 of the LAG-3 protein, SEQ ID NO. 7). Moreover, the LAG-3 gene has been localized on chromosome 12 (band p 13.3) (Triebel (28)) close to CD4. The study of human-hamster hybrid cells has shown that cell proteins encoded in genes of the human chromosome 12 (genes different from CD4) were necessary and sufficient for the expression of the HIV genes (Hart (29)). The LAG-3 protein might thus be involved in the reproductive cycle of the HIV, resulting in the production of infectious virions, independently of its possible capacity to act as receptor for the HIV.

Finally, structural homologies exist between the cytoplasmic region of the LAG-3 protein (in particular in the region of the peptide Arg Arg Gln Trp Arg Pro Arg Arg Phe Ser corresponding to amino acid residues 447 to 456 of SEQ ID NO:7) and various proteins encoded in the HIV genome, such as for example the REV protein (Yourno (30)) or FIV (Ratner (31)). These homology relationships suggest there again that the LAG-3 protein expressed by activated lymphocytes might play a role in the phases of replication or in the production of infectious viral particles of the HIV.

IX—Detection of the Natural LAG-3 Molecule

Anti-LAG-3 rabbit antibodies were obtained after repeated injections of a synthetic peptide coupled to KLH into rabbits. This peptide comprises 30 amino acids forming the sequence shown in the sequence SEQ ID NO 3 included in the extra loop of domain V of LAG-3.

After labelling of the membrane proteins of T cells activated by phytohemagglutinin with $^{125}I$, immunoprecipitation by specific rabbit antibodies and purification on SDS-polyacrylamide gel, a single band of about 55 k daltons was detected under reducing and non-reducing conditions (FIG. 7). This observed molecular mass of about 55 k daltons would correspond to the molecular mass derived from the analysis of the translation of the LAG-3 protein (51 k daltons) to which are added about 5 k daltons due to the presence of sugars (in particular at some of the 4 N-glycosylation sites), making the natural LAG-3 protein a membrane glycoprotein.

The LAG-3 protein does exist in the form of a single chain, probably glycosylated, at the surface of the T cells.

X—In vitro Transcription and Translation of the LAG-3 Gene

In order to conclusively define the coding region and establish the capacity to be translated of the mRNA obtained by transcription of the FDC sequence, we have transcribed both strands of the FDC cDNA (Eco 47 III - Bgl II 209–1829 bp fragment) by using either the T3 or the T7 RNA polymerase using as substrate the FDC clone in the pBS vector. The two RNA preparations were then translated in vitro by using a rabbit reticulocyte extract in the presence of methionine $^{35}S$. The sense RNA containing the poly-A tail at the 3' end was translated into a protein of molecular mass of 55,000 daltons which could be detected by autoradiography after migration in a gel of the SDS-PAGE type. This estimated molecular mass is very similar to the theoretical molecular mass of 54457 corresponding to the 498 amino acids of the LAG-3 polypeptide with an intact, uncleaved signal peptide. No translation product larger than 20,000 daltons could be detected using the anti-sense LAG-3 RNA as substrate in the reaction with the rabbit reticulocyte extract.

XI—Expression of a Transmembrane Recombinant LAG-3 Protein (LAG 3-C) and a Soluble Recombinant LAG-3 Protein (LAG 3-S)

We have employed a system using a vector of the "baculovirus" type. This system makes it possible to produce proteins of an insect (Spodoptera Frugiperda) foreign to the cells (SF9 cells) by using in vivo recombination between a transfer vector (plasmid p PVL 941) which contains the foreign gene, on the one hand, and the genome of a virus (Autographa Californica Nuclear Polyhedrosis virus AcMNPV), on the other. The viral genome is placed under the strong control of the promoter for the gene of the protein called polyhedrin. This system was described by Luckow (21) after transfection of the recombinant plasmid and the viral genome; the SF9 cells are selected by successive purifications (screening of recombinants), thus making possible the production of considerable amounts of recombinant protein. This protein is normally cleaved (the hydrophobic signal peptide is removed inside the cell) and glycosylated (at least partially).

1) Construction of the transfer vector a) Preparation of the vector

The schema for the preparation of the vector is shown in FIG. 8.

The vector PVL941 (obtainable from Dr. Max SUMMERS, University of Texas, U.S.A.) was cut by the restriction enzyme BamHI, then dephosphorylated by calf intestine phosphatase. This was done in order to prevent the autoligation of the vector with itself.

We then prepared from the FDC cDNA clone a fragment of 1620 base pairs resulting from digestion by the enzymes EC047 III (position 209 of FDC) and BglII (position 1829 of FDC). The ends cut; on the one hand, by the enzyme Eco47III and by the enzyme BglII on the other, were made blunt by a synthetic reaction with a Klenow DNA polymerase (T4 DNA polymerase). A double-stranded oligonucleotide "linker" containing a BglII restriction site was then attached to the Eco47III BglII FDC fragment in order to create the construction LAG 3-C (C for complete) and a linker containing a BamHI site was attached in order to create the construction LAG 3-S (S for soluble). After ligation, digestion was performed with an excess of restriction enzyme of the BglII type (in the case of the construction LAG 3-C) or of the BamHI type (in the case of the construction LAG 3-S), then the fragments corresponding to the 2 constructions were purified by gel electrophoresis. The last step consisted of linking the BglII LAG 3-C fragment or the BamHI LAG 3-S fragment to the vector PVL 941-BamHI.

b) Selection and amplification of the recombinant vectors Competent JM109 bacteria were transformed with the recombinant transfer vector containing one or other of the constructions. Colonies resistant to ampicillin were placed in culture, then the plasmid DNA contained in these bacteria was purified; in this way, a number of clones containing the transfer vector was obtained and clones containing the LAG 3-C fragment or the LAG 3-S fragment in the right orientation were selected. In order to obtain the recombined plasmid in the pure state, capable of being used in transfection experiments, the clone of bacteria thus obtained was placed in culture in 500 ml of medium with ampicillin, then the plasmid was purified on a cesium chloride gradient.

c) Purification of genomic DNA of the virus

This was done according to the method described in "A manual of methods for Baculovirus vectors and insect cell culture procedures" provided by Dr. Max SUMMERS of the University of Texas, U.S.A.

d) Transfection of cells with the recombinant vector containing the LAG 3-C or LAG 3-S insert and the genome of the virus.

It concerns the co-transfection of SF9 cells with, on the one hand, the purified recombinant vector and the viral genome on the other using the calcium chloride method. This was done in accordance with the conditions described in the manual referred to in.c).

e) Selection of the recombined viruses

5 Days after transfection, the supernatants of the SF9 cells were recovered, then assayed. These assays are performed by infecting fresh SF9 cells with successive dilutions of this primary culture supernatant. Initially, there are considered to be $10^7$ pfu/ml (pfu ="plaque forming unit") and successive dilutions are made so as to obtain between 100 and 1 pfu/ml. After 3 days, the SF9 cells thus infected are assayed by the "dot blot" hybridization procedure. The cells are lysed with NaOH, transferred to nylon and hybridized with a probe corresponding to the FDC fragment of 1871 base pairs. After washing and autoradiography, the positive wells are located and the wells corresponding to the highest dilutions are retained. This screening technique is performed a second and third time. During the third screening, a check is made that the dots giving a positive signal in "dot blot" hybridization do not contain SF9 cells containing inclusions. These inclusions correspond to the secretion of the protein polyhedrin, produced after infection of SF9 cells by a non-recombined, wild-type virus. This last point was also checked not by direct reading of the plaque but by a procedure involving collection of the cells, spreading them on a glass slide and staining with May-Grünwald-Giemsa.

f) Detection of the recombinant protein LAG 3-C and LAG 3-S

Figure 9:
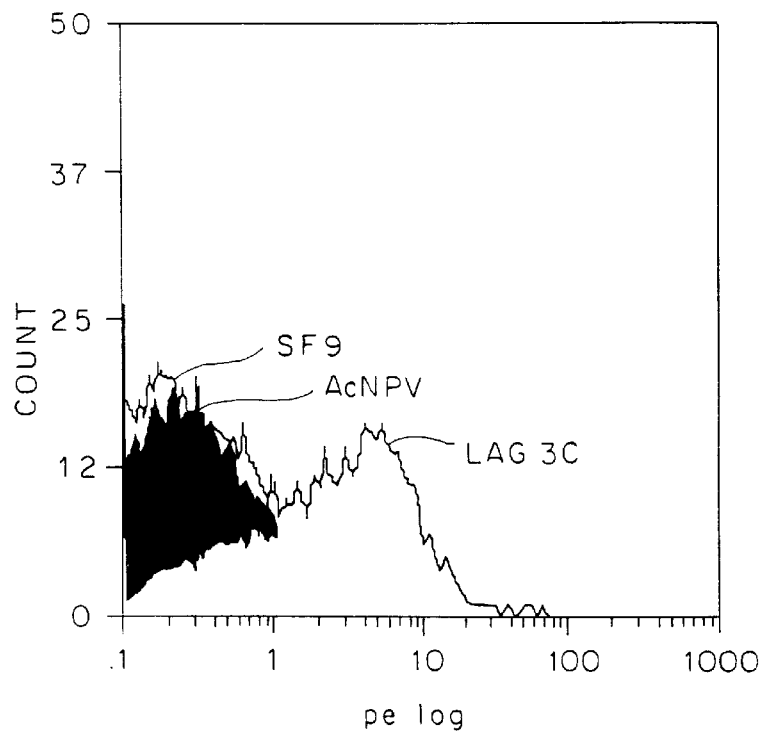
FIG. 9 presents the result of the detection by immofluorescence of LAG-3C in the baculovirus system by means of a heteroantiserum.
Figure 10:
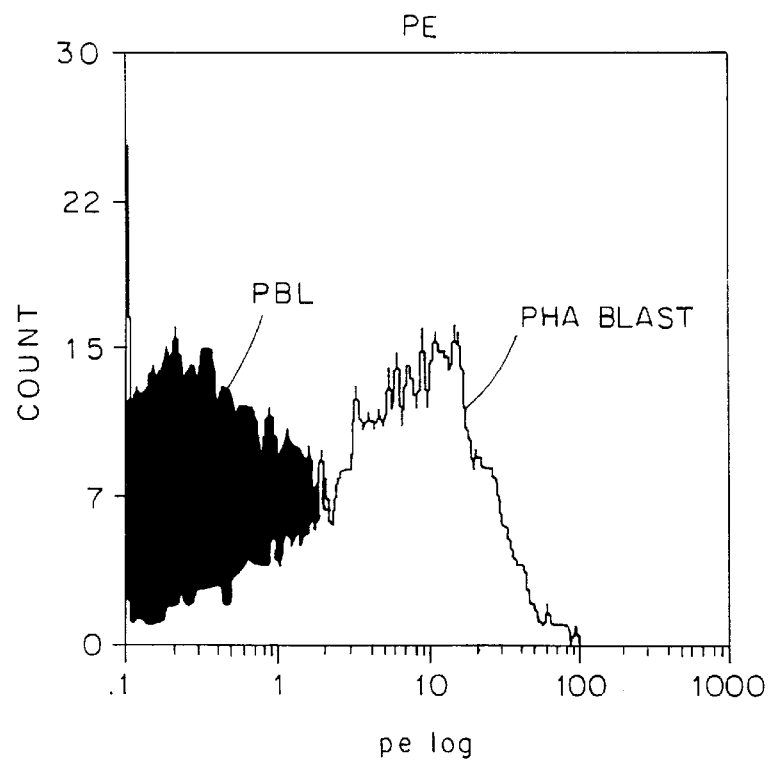
FIG. 10 shows by immunofluorescence the reactivity of a heteroantiserum on PHA-blasts and PBL.

SF9 cells infected with the recombinant viral clone containing the LAG 3-C fragment were obtained on the 5th day of culture after an infection at 0.1 pfu/cell. These SF9 cells express the recombinant LAG-3 molecule at the surface as is shown by the immunofluorescent reactivity of the specific rabbit antibody, compared with the reactivity obtained with uninfected SF9 cells or SF9 cells infected with a AcNPV wild-type virus (FIG. 9). Furthermore, the reactivity of the LAG-3-specific rabbit serum towards the SF9 cells expressing LAG-3 was compared with the reactivity obtained towards T lymphocytes activated by phytohemagglutinin (PHA-blasts). The histograms obtained are similar and thus show that the number of recombinant LAG-3 molecules (FIG. 9) expressed at the surface of the SF9 cells is comparable to the number of natural LAG-3 molecules expressed at the surface of the activated lymphocytes (FIG. 10).

Figure 11:
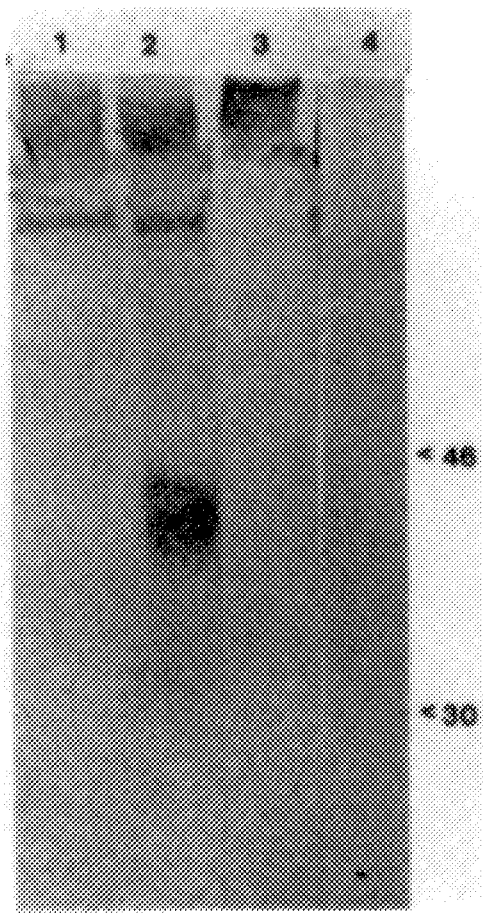
FIG. 11 presents the result of the detection of LAG-3S in the baculovirus system by means of a heteroantiserum in a Western blot.

Supernatants of SF9 cells infected with the recombinant viral clone containing the LAG 3-S fragment were obtained on the 5th day of culture after an infection at 0.1 pfu/cell. A supernatant was assayed by the so-called "western blot" technique with the anti-loop anti-peptide antibodies of domain V described in section IX. A pure signal corresponding to a protein of about 45 kd was obtained after revelation with anti-rabbit goat antibodies labelled with peroxidase (FIG. 11).

This molecular mass corresponds well with the mass expected of the LAG 3-S Eco47 III-BamHI fusion protein (38038K daltons) after glycosylation in the SF9 cells.

The structure of the part coding for LAG 3-S (SEQ ID No.5) shows that the first three domains of LAG-3 (upstream from the internal BamHI site) were fused with a nucleotide segment of 56 base pairs of the gene for polyhedrin downstream from the BamHI site. In total, after cleavage of the signal peptide of 28 amino acids, the fusion protein comprises 352 amino acids, 335 corresponding to LAG-3 and 17 being derived from one of the reading frames of the gene for polyhedrin.

REFERENCES

1. Nowill, A. et al., J. Exp. Med. 163, 1601.
2. Maniatis, T. et al., 1982. Molecular cloning: A laboratory manual, Cold spring harbor laboratory New York.
3. Mechler, B. et al., J. Cell Biol. 88, 29 (1981).
4. Aviv et al., Proc. Natl. Acad. Sci. USA 69: 1408.
5. Triebel, F. et al., Eur. J. Immunol. 17, 1209.
6. Gubler, U. et al., Gene. 25, 263.
7. Davis, M. M. et al., Proc. Natl. Acad. Sci. USA. 81:2194.
8. Huynh, T. V. et al., DNA cloning: A practical approach. 49–78, D. Glover Editor. IRL Press. Oxford. United Kingdom.
9. Sanger, F. et al., Proc. Natl. Acad. Sci. USA 75, 5463.
10. Dariavach, P. et al., Proc. Natl. Acad. Sci. USA. 84, 9074.
11. Feinberg, A. P. et al., Anal. Biochem. 132, 6.
12. Amzel, L. M. et al., Ann. Rev. Biochem 48, 961 (1979).
13. Williams, A. F. Immunol. Today 8, 298 (1987).
14. Lesk, A. M. & Chothia, C. J. Mol. Biol. 160, 325 (1982).
15. Santoni, M. J. et al. EMBO J. 8, 395 (1989).
16. Kirszbaum, L. et al., J. Immunol. 142, 3931 (1989) .
17. Ruoslahti, E. et al., M. D. Cell 44, 517 (1986).
18. Dayhoff, M. O. et al., Enzymol. 91, 524 (1983).
19. Williams, A. F. et al., Ann. Rev. Immunol. 6, 381.
20. Maddon, P. J. et al. Proc. Natl. Acad. Sci. USA 84, 9155 (1987).
21. Luckow, V. A. et al., Bio/Technology, 6:47.
22. Ryu S. E. et al., Nature, 348, 419.
23. Wang J. et al., Nature, 348, 411
24. Byrn R. A. et al., Nature 344, 667
25. Staunton D. E. et al., Cell. 61, 243
26. Wegner C. D. et al., Science 247, 456
27. Marlin S. D. et al., Nature 344, 70
28. Triebel F. et al;, J. Exp. Med., 171, 1393
29. Hart E. C. et al., Science, 240, 488
30. Yourno J. et al., AIDS Res. Hum. Retroviruses 4:165–173(1988).

31. Ratner L. et al., Nature 313:277–284 (1985).

| Symbols of the amino acids | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |

-continued

| Symbols of the amino acids | | |
|---|---|---|
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

We claim:

1. An isolated DNA segment comprising a DNA sequence encoding the extracellular domain of LAG-3 protein having the amino acid sequence of residues 1 to 420 of SEQ ID NO:7.

2. The isolated DNA segment according to claim 1, wherein said amino acid sequence is amino acid residues 1 to 420 of SEQ ID NO:7 with an added methionine residue immediately N-terminal to amino acid residue 1 of SEQ ID NO:7.

3. An expression vector comprising a isolated DNA segment according to claim 1.

4. A host cell transformed with a vector according to claim 3.

5. A process for the production of a protein comprising the extracellular domain of LAG-3 protein, comprising the steps of:

expressing the protein comprising the extracellular domain or LAG-3 protein in the host cell of claim 4; and collecting the protein which is expressed.

6. An isolated DNA segment comprising a DNA sequence encoding a peptide having an amino acid sequence selected from the group consisting of amino acid residues 1 to 142 of SEQ ID NO:7, amino acid residues 143 to 232 of SEQ ID NO:7, amino acid residues 233 to 342 of SEQ ID NO:7, amino acid residues 343 to 413 of SEQ ID NO:7, and amino acid residues 42–71 of SEQ ID NO:7.

7. The isolated DNA segment according to claim 6, wherein said amino acid sequence is amino acid residues 1 to 142 of SEQ ID NO:7 with an added methionine residue immediately N-terminal to amino acid residue 1 of SEQ ID NO:7.

8. An expression vector comprising a isolated DNA segment according to claim 6.

9. A host cell transformed with a vector according to claim 8.

10. A process for the production of a protein comprising the extracellular domain of LAG-3 protein, comprising the steps of:

expressing the protein comprising the extracellular domain of LAG-3 protein in the host cell of claim 9; and collecting the protein which is expressed.

* * * * *